US010188614B2

(12) United States Patent
York et al.

(10) Patent No.: US 10,188,614 B2
(45) Date of Patent: *Jan. 29, 2019

(54) PARTICULATE MATERIALS

(71) Applicant: Nektar Therapeutics, San Francisco, CA (US)

(72) Inventors: Peter York, Illkley (GB); Boris Yu Shekunov, Aurora, OH (US); Mahboob Ur Rehman, Leeds (GB); Jane Catherine Feeley, Bradford (GB)

(73) Assignee: Nektar Therapeutics, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/619,139

(22) Filed: Jun. 9, 2017

(65) Prior Publication Data

US 2017/0273920 A1 Sep. 28, 2017

Related U.S. Application Data

(63) Continuation of application No. 15/098,183, filed on Apr. 13, 2016, now Pat. No. 9,700,529, which is a continuation of application No. 13/622,272, filed on Sep. 18, 2012, now Pat. No. 9,339,459, which is a continuation of application No. 10/422,342, filed on Apr. 24, 2003, now Pat. No. 8,273,330.

(30) Foreign Application Priority Data

| May 3, 2002 | (GB) | 0210174.9 |
| May 7, 2002 | (GB) | 0210268.9 |
| May 15, 2002 | (GB) | 0211086.4 |
| Jul. 17, 2002 | (GB) | 0216562.9 |

(51) Int. Cl.
| A61K 31/137 | (2006.01) |
| A61K 31/48 | (2006.01) |
| A61K 31/485 | (2006.01) |
| A61K 31/4985 | (2006.01) |
| A61K 9/16 | (2006.01) |
| A61K 9/00 | (2006.01) |
| A61M 15/00 | (2006.01) |

(52) U.S. Cl.
CPC .......... *A61K 31/137* (2013.01); *A61K 9/0075* (2013.01); *A61K 9/16* (2013.01); *A61K 9/1688* (2013.01); *A61K 31/48* (2013.01); *A61K 31/485* (2013.01); *A61K 31/4985* (2013.01); *A61M 15/0091* (2013.01); *A61M 2202/064* (2013.01)

(58) Field of Classification Search
None
See application file for complete search history.

(56) References Cited

U.S. PATENT DOCUMENTS

| 2,598,525 A | 4/1950 | Fox |
| 3,362,405 A | 1/1968 | Hazel |
| 3,425,600 A | 2/1969 | Abplanalp |
| 3,674,901 A | 7/1972 | Shepherd et al. |
| 3,770,207 A | 11/1973 | Muller et al. |
| 3,790,079 A | 2/1974 | Berglund et al. |
| 3,825,188 A | 7/1974 | Doering |
| 3,921,637 A | 11/1975 | Bennie et al. |
| 3,964,483 A | 6/1976 | Mathes |
| 3,991,304 A | 11/1976 | Hillsman |
| 3,991,761 A | 11/1976 | Cocozza |
| 3,994,421 A | 11/1976 | Hansen |
| 4,035,317 A | 7/1977 | Gershberg |
| 4,036,223 A | 7/1977 | Obert |
| 4,052,255 A | 10/1977 | Hackbarth et al. |
| 4,069,819 A | 1/1978 | Valentini et al. |
| 4,098,273 A | 7/1978 | Glenn |
| 4,127,235 A | 11/1978 | Klaile et al. |
| 4,153,689 A | 5/1979 | Hirai et al. |
| 4,211,769 A | 7/1980 | Okada et al. |
| 4,221,339 A | 9/1980 | Yoshikawa |
| 4,249,526 A | 2/1981 | Dean et al. |
| 4,253,468 A | 3/1981 | Lehmbeck |
| 4,261,793 A | 4/1981 | Nakamura et al. |
| 4,294,624 A | 10/1981 | Veltman |
| 4,294,829 A | 10/1981 | Suzuki et al. |
| 4,305,210 A | 12/1981 | Christensen et al. |
| 4,338,931 A | 7/1982 | Cavazza |
| 4,341,759 A | 7/1982 | Bogentoft et al. |
| 4,397,907 A | 8/1983 | Rosser et al. |
| 4,423,099 A | 12/1983 | Mueller et al. |

(Continued)

FOREIGN PATENT DOCUMENTS

| DE | 1078283 | 3/1960 |
| DE | 2209477 A | 9/1973 |

(Continued)

OTHER PUBLICATIONS

Al-Omran et al., "Formulation and Physicochemical Evaluations of Diclofenac Sodium Chewable Tablets", Saudi Pharmaceutical J., 10(4)177-183, (2002).

(Continued)

*Primary Examiner* — Michael P Cohen

(74) *Attorney, Agent, or Firm* — Susan T. Evans

(57) ABSTRACT

The present invention relates to active substances in particulate form, to methods for preparing them and to their uses. The present invention provides particulate powders, such as might be of use for delivery using a dry powder inhaler (DPI) or similar delivery device, having properties which may be beneficial to the DPI delivery process.

41 Claims, 10 Drawing Sheets

(56) References Cited

U.S. PATENT DOCUMENTS

| | | |
|---|---|---|
| 4,446,862 A | 5/1984 | Baum et al. |
| 4,452,239 A | 6/1984 | Malem |
| 4,476,804 A | 10/1984 | Glatt et al. |
| 4,484,577 A | 11/1984 | Sackner et al. |
| 4,486,435 A | 12/1984 | Schmidt et al. |
| 4,503,035 A | 3/1985 | Pestka et al. |
| 4,514,574 A | 4/1985 | Inoue et al. |
| 4,534,343 A | 8/1985 | Nowacki et al. |
| 4,540,602 A | 9/1985 | Motoyama et al. |
| 4,582,731 A | 4/1986 | Smith |
| 4,590,206 A | 5/1986 | Forrester et al. |
| 4,624,251 A | 11/1986 | Miller |
| 4,624,848 A | 11/1986 | Lee |
| 4,627,432 A | 12/1986 | Newell et al. |
| 4,649,911 A | 3/1987 | Knight et al. |
| 4,659,696 A | 4/1987 | Hirai et al. |
| 4,677,975 A | 7/1987 | Edgar et al. |
| 4,698,328 A | 10/1987 | Neer et al. |
| 4,702,799 A | 10/1987 | Tuot |
| 4,721,709 A | 1/1988 | Seth et al. |
| 4,739,754 A | 4/1988 | Shaner |
| 4,748,034 A | 5/1988 | De Rham |
| 4,760,093 A | 7/1988 | Blank et al. |
| 4,784,878 A | 11/1988 | Haak |
| 4,790,305 A | 12/1988 | Zoltan et al. |
| 4,794,167 A | 12/1988 | Linder et al. |
| 4,807,814 A | 2/1989 | Douche et al. |
| 4,811,731 A | 3/1989 | Newell et al. |
| 4,818,424 A | 4/1989 | Evans et al. |
| 4,819,629 A | 4/1989 | Jonson |
| 4,823,784 A | 4/1989 | Bordoni et al. |
| 4,833,125 A | 5/1989 | Neer et al. |
| 4,835,187 A | 5/1989 | Reuter et al. |
| 4,866,051 A | 9/1989 | Hunt et al. |
| 4,871,489 A | 10/1989 | Ketcham |
| 4,884,565 A | 12/1989 | Cocozza |
| 4,889,114 A | 12/1989 | Kladders |
| 4,898,781 A | 2/1990 | Onouchi et al. |
| 4,907,583 A | 3/1990 | Wetterlin et al. |
| 4,919,853 A | 4/1990 | Alvarez et al. |
| 4,923,720 A | 5/1990 | Lee et al. |
| 4,926,852 A | 5/1990 | Zoltan et al. |
| 4,942,544 A | 7/1990 | McIntosh et al. |
| 4,946,828 A | 8/1990 | Markussen |
| 4,952,402 A | 8/1990 | Sparks et al. |
| 4,968,607 A | 11/1990 | Dower et al. |
| 4,984,158 A | 1/1991 | Hillsman |
| 4,995,385 A | 2/1991 | Valentini et al. |
| 4,999,189 A | 3/1991 | Kogan et al. |
| 5,000,888 A | 3/1991 | Kilbride, Jr. et al. |
| 5,009,367 A | 4/1991 | Nielsen |
| 5,011,678 A | 4/1991 | Wang et al. |
| 5,017,372 A | 5/1991 | Hastings |
| 5,026,550 A | 6/1991 | Aeschbach et al. |
| 5,027,806 A | 7/1991 | Zoltan et al. |
| 5,033,463 A | 7/1991 | Cocozza |
| 5,035,237 A | 7/1991 | Newell et al. |
| 5,038,769 A | 8/1991 | Krauser |
| 5,042,975 A | 8/1991 | Chien et al. |
| 5,043,280 A | 8/1991 | Fischer et al. |
| 5,048,514 A | 9/1991 | Ramella |
| 5,049,388 A | 9/1991 | Knight et al. |
| 5,066,522 A | 11/1991 | Cole et al. |
| 5,081,228 A | 1/1992 | Dower et al. |
| 5,093,316 A | 3/1992 | Lezdey et al. |
| 5,098,893 A | 3/1992 | Franks et al. |
| 5,099,833 A | 3/1992 | Michaels |
| 5,113,855 A | 5/1992 | Newhouse |
| 5,139,016 A | 8/1992 | Waser |
| 5,161,524 A | 11/1992 | Evans |
| 5,178,878 A | 1/1993 | Wehling et al. |
| 5,180,812 A | 1/1993 | Dower et al. |
| 5,186,164 A | 2/1993 | Raghuprasad |
| 5,196,575 A | 3/1993 | Sebastian |
| 5,200,399 A | 4/1993 | Wettlaufer et al. |
| 5,204,108 A | 4/1993 | Illum |
| 5,219,120 A | 6/1993 | Ehrenberg et al. |
| 5,219,575 A | 6/1993 | Van Bommel et al. |
| 5,221,731 A | 6/1993 | Weymans et al. |
| 5,229,486 A | 7/1993 | Paul et al. |
| 5,230,884 A | 7/1993 | Evans et al. |
| 5,232,707 A | 8/1993 | Lokensgard |
| 5,254,330 A | 10/1993 | Ganderton et al. |
| 5,260,306 A | 11/1993 | Boardman et al. |
| 5,269,980 A | 12/1993 | Levendis et al. |
| 5,279,708 A | 1/1994 | Wood et al. |
| 5,290,765 A | 3/1994 | Wettlaufer et al. |
| 5,295,479 A | 3/1994 | Lankinem |
| 5,302,581 A | 4/1994 | Sarin et al. |
| 5,309,900 A | 5/1994 | Knoch et al. |
| 5,320,094 A | 6/1994 | Laube et al. |
| 5,320,714 A | 6/1994 | Brendel |
| 5,331,953 A | 7/1994 | Andersson et al. |
| 5,354,562 A | 10/1994 | Platz et al. |
| 5,354,934 A | 10/1994 | Pitt et al. |
| 5,364,838 A | 11/1994 | Rubsamen |
| 5,376,359 A | 12/1994 | Johnson |
| 5,376,386 A | 12/1994 | Ganderton et al. |
| 5,384,133 A | 1/1995 | Boyes et al. |
| 5,424,076 A | 6/1995 | Gorissen et al. |
| 5,458,135 A | 10/1995 | Patton et al. |
| 5,482,927 A | 1/1996 | Maniar et al. |
| 5,506,203 A | 4/1996 | Backstrom et al. |
| 5,510,118 A | 4/1996 | Bosch et al. |
| 5,518,187 A | 5/1996 | Bruno et al. |
| 5,518,709 A | 5/1996 | Sutton et al. |
| 5,518,998 A | 5/1996 | Backstrom et al. |
| 5,548,004 A | 8/1996 | Mandel et al. |
| 5,554,382 A | 9/1996 | Castor |
| 5,580,856 A | 12/1996 | Prestreslki et al. |
| 5,607,697 A | 3/1997 | Alkire et al. |
| 5,622,657 A | 4/1997 | Takada et al. |
| 5,624,530 A | 4/1997 | Sadykhov et al. |
| 5,628,937 A | 5/1997 | Oliver et al. |
| 5,639,475 A | 6/1997 | Bettman et al. |
| 5,648,096 A | 7/1997 | Gander et al. |
| 5,651,990 A | 7/1997 | Takada et al. |
| 5,667,806 A | 9/1997 | Kantor |
| 5,687,905 A | 11/1997 | Tsai |
| 5,708,039 A | 1/1998 | Daly et al. |
| 5,709,886 A | 1/1998 | Bettman et al. |
| 5,716,558 A | 2/1998 | Nielsen et al. |
| 5,723,269 A | 3/1998 | Akagi et al. |
| 5,725,836 A | 3/1998 | Rouanet et al. |
| 5,727,333 A | 3/1998 | Folan |
| 5,741,478 A | 4/1998 | Osbome et al. |
| 5,776,491 A | 7/1998 | Allen, Jr. et al. |
| 5,795,594 A | 8/1998 | York et al. |
| 5,800,598 A | 9/1998 | Chein et al. |
| 5,807,576 A | 9/1998 | Allen, Jr. et al. |
| 5,807,578 A | 9/1998 | Acosta-Cuello et al. |
| 5,851,453 A | 12/1998 | Hanna et al. |
| 5,874,029 A | 2/1999 | Subramaniam et al. |
| 5,874,064 A | 2/1999 | Edwards et al. |
| 5,916,596 A | 6/1999 | Desai et al. |
| 5,924,216 A | 7/1999 | Takahashi |
| 5,952,008 A | 9/1999 | Backstrom et al. |
| 5,964,416 A | 10/1999 | Jaeger et al. |
| 5,970,974 A | 10/1999 | Van Der Linden et al. |
| 5,976,574 A | 11/1999 | Gordon |
| 5,985,248 A | 11/1999 | Gordon et al. |
| 5,985,309 A | 11/1999 | Edwards et al. |
| 5,993,805 A | 11/1999 | Sutton et al. |
| 5,997,848 A | 12/1999 | Patton et al. |
| 6,001,336 A | 12/1999 | Gordon |
| 6,015,546 A | 1/2000 | Sutton et al. |
| 6,017,310 A | 1/2000 | Johnson |
| 6,022,525 A | 2/2000 | Sutton et al. |
| 6,051,256 A | 4/2000 | Platz et al. |
| 6,051,257 A | 4/2000 | Kodas et al. |
| 6,063,138 A | 5/2000 | Hanna et al. |
| 6,077,543 A | 6/2000 | Gordon et al. |
| 6,116,516 A | 9/2000 | Ganan-Calvo |
| 6,123,924 A | 9/2000 | Mistry et al. |

(56) References Cited

U.S. PATENT DOCUMENTS

| | | | |
|---|---|---|---|
| 6,149,941 A | 11/2000 | Schwarz et al. | |
| 6,153,129 A | 11/2000 | Herbert et al. | |
| 6,156,511 A | 12/2000 | Schatz et al. | |
| 6,174,469 B1 | 1/2001 | Ganan-Calvo | |
| 6,197,835 B1 | 3/2001 | Ganan-Calvo | |
| 6,258,341 B1 | 7/2001 | Foster et al. | |
| 6,290,991 B1 | 9/2001 | Roser et al. | |
| 6,308,434 B1 | 10/2001 | Chickering, III et al. | |
| 6,316,029 B1 | 11/2001 | Jain et al. | |
| 6,322,897 B1 | 11/2001 | Borchert et al. | |
| 6,331,290 B1 | 12/2001 | Morgan | |
| 6,331,310 B1 | 12/2001 | Roser et al. | |
| 6,365,190 B1 | 4/2002 | Gordon et al. | |
| 6,387,410 B1 | 5/2002 | Woolfe et al. | |
| 6,414,050 B1 | 7/2002 | Howdle et al. | |
| 6,416,739 B1 | 7/2002 | Rogerson et al. | |
| 6,423,344 B1 | 7/2002 | Platz et al. | |
| 6,455,028 B1 | 9/2002 | Wulffhart et al. | |
| 6,503,480 B1 | 1/2003 | Edwards et al. | |
| 6,518,239 B1 | 2/2003 | Kuo et al. | |
| 6,551,617 B1 | 4/2003 | Howdle et al. | |
| 6,565,885 B1 | 5/2003 | Tarara et al. | |
| 6,572,893 B2 | 6/2003 | Gordon et al. | |
| 6,582,728 B1 | 6/2003 | Platz et al. | |
| 6,592,904 B2 | 7/2003 | Platz et al. | |
| 6,656,492 B2 | 12/2003 | Kaliyama et al. | |
| 6,660,382 B2 | 12/2003 | Nouri et al. | |
| 6,860,907 B1 | 3/2005 | Hanna et al. | |
| 6,884,408 B2 | 4/2005 | Rabinowitz et al. | |
| 6,977,087 B2 | 12/2005 | Edwards et al. | |
| 8,273,330 B2 * | 9/2012 | York | A61K 9/1688 424/46 |
| 9,339,459 B2 * | 5/2016 | York | A61K 9/0075 |
| 9,700,529 B2 * | 7/2017 | York | A61K 31/137 |
| 2002/0000681 A1 | 1/2002 | Gupta et al. | |
| 2002/0017295 A1 | 2/2002 | Weers et al. | |
| 2002/0071871 A1 | 6/2002 | Snyder et al. | |
| 2002/0081266 A1 | 6/2002 | Woolfe et al. | |
| 2002/0114844 A1 | 8/2002 | Hanna et al. | |
| 2002/0175225 A1 | 11/2002 | Boersen et al. | |
| 2003/0047824 A1 | 3/2003 | Hanna et al. | |
| 2003/0109421 A1 | 6/2003 | Palakodaty et al. | |
| 2003/0124193 A1 | 7/2003 | Snyder et al. | |
| 2003/0170310 A1 | 9/2003 | Wadhwa | |
| 2003/0175214 A1 | 9/2003 | Staniforth et al. | |
| 2003/0203036 A1 | 10/2003 | Gordon et al. | |
| 2003/0215514 A1 | 11/2003 | Platz et al. | |
| 2004/0071783 A1 | 4/2004 | Hanna et al. | |
| 2004/0119179 A1 | 6/2004 | Perrut et al. | |
| 2005/0170000 A1 | 8/2005 | Walker et al. | |
| 2005/0206023 A1 | 9/2005 | Hanna et al. | |
| 2016/0324806 A1 | 11/2016 | York et al. | |

FOREIGN PATENT DOCUMENTS

| | | |
|---|---|---|
| DE | 4041563 | 6/1992 |
| EP | 0072046 | 2/1983 |
| EP | 0122036 | 10/1984 |
| EP | 0237507 | 9/1987 |
| EP | 0322687 | 7/1989 |
| EP | 0344375 | 12/1989 |
| EP | 0347779 | 12/1989 |
| EP | 0360340 | 3/1990 |
| EP | 0383569 | 8/1990 |
| EP | 0408801 | 1/1991 |
| EP | 0461930 | 12/1991 |
| EP | 0464171 | 1/1992 |
| EP | 0467172 | 1/1992 |
| EP | 0468914 | 1/1992 |
| EP | 469725 | 2/1992 |
| EP | 0490797 | 6/1992 |
| EP | 0506293 | 9/1992 |
| EP | 512693 | 11/1992 |
| EP | 0542314 | 5/1993 |
| EP | 0611567 | 8/1994 |
| EP | 628331 | 12/1994 |
| EP | 0661091 | 7/1995 |
| EP | 674541 | 10/1995 |
| EP | 0677332 | 10/1995 |
| EP | 681843 | 11/1995 |
| EP | 709085 | 5/1996 |
| EP | 899017 | 3/1999 |
| EP | 972526 | 1/2000 |
| EP | 1004349 | 5/2000 |
| EP | 1022020 | 7/2000 |
| FR | 2257351 | 8/1975 |
| GB | 473471 | 10/1937 |
| GB | 621785 | 4/1949 |
| GB | 1527605 | 8/1975 |
| GB | 2105189 | 3/1983 |
| GB | 2322326 | 8/1998 |
| GB | 2371501 | 7/2002 |
| GB | 0300338.1 | 7/2004 |
| GB | 0300339.9 | 9/2005 |
| JP | 7242568 | 9/1995 |
| JP | 8067666 | 3/1996 |
| JP | 9082319 A | 3/1997 |
| KR | 9611238 A | 8/1996 |
| NL | 7712041 | 5/1979 |
| SU | 0628930 | 10/1978 |
| SU | 1003926 | 1/1979 |
| WO | WO 81/02975 | 10/1981 |
| WO | WO 88/04556 | 6/1988 |
| WO | WO 88/07870 | 10/1988 |
| WO | WO 88/09163 | 12/1988 |
| WO | WO 90/03782 | 4/1990 |
| WO | WO 90/07351 | 7/1990 |
| WO | WO 90/09780 | 9/1990 |
| WO | WO 90/11139 | 10/1990 |
| WO | WO 90/15635 | 12/1990 |
| WO | WO 91/02545 | 3/1991 |
| WO | WO 91/02558 | 3/1991 |
| WO | WO 91/16882 | 11/1991 |
| WO | WO 92/18164 | 10/1992 |
| WO | WO 93/02712 | 2/1993 |
| WO | WO 93/07465 | 4/1993 |
| WO | WO 93/09832 | 5/1993 |
| WO | WO 94/07514 | 4/1994 |
| WO | WO 94/08552 | 4/1994 |
| WO | WO 94/08627 | 4/1994 |
| WO | WO 95/00127 | 1/1995 |
| WO | WO 95/00128 | 1/1995 |
| WO | WO 95/01221 | 1/1995 |
| WO | WO 95/01324 | 1/1995 |
| WO | WO 95/13864 | 5/1995 |
| WO | WO 95/21688 | 8/1995 |
| WO | WO 95/23613 | 9/1995 |
| WO | WO 95/24183 | 9/1995 |
| WO | WO 95/31479 | 11/1995 |
| WO | WO 96/00610 | 1/1996 |
| WO | WO 96/03978 | 2/1996 |
| WO | WO 96/05809 | 2/1996 |
| WO | WO 96/09814 | 4/1996 |
| WO | WO 96/11580 | 4/1996 |
| WO | WO 96/15814 | 5/1996 |
| WO | WO 96/32096 | 10/1996 |
| WO | WO 96/32149 | 10/1996 |
| WO | WO 97/03649 | 2/1997 |
| WO | WO 97/14407 | 4/1997 |
| WO | WO 97/28788 | 8/1997 |
| WO | WO 97/31691 | 9/1997 |
| WO | WO 97/36574 | 10/1997 |
| WO | WO 97/36578 | 10/1997 |
| WO | WO 97/41833 | 11/1997 |
| WO | WO 97/44067 | 11/1997 |
| WO | WO 98/01228 | 1/1998 |
| WO | WO 98/13136 | 4/1998 |
| WO | WO 98/17676 | 4/1998 |
| WO | WO 98/29096 | 7/1998 |
| WO | WO 98/29098 | 7/1998 |
| WO | WO 98/31346 | 7/1998 |
| WO | WO 98/36825 | 8/1998 |
| WO | WO 98/46215 | 10/1998 |

(56) References Cited

FOREIGN PATENT DOCUMENTS

| WO | WO 98/47493 | 10/1998 |
|----|----|----|
| WO | WO 98/52544 | 11/1998 |
| WO | WO 99/16419 | 4/1999 |
| WO | WO 99/16422 | 4/1999 |
| WO | WO 99/17742 | 4/1999 |
| WO | WO 99/17748 | 4/1999 |
| WO | WO 99/30834 | 6/1999 |
| WO | WO 99/31019 | 6/1999 |
| WO | WO 99/32083 | 7/1999 |
| WO | WO 99/59710 | 11/1999 |
| WO | WO 99/64014 | 12/1999 |
| WO | WO 00/00176 | 1/2000 |
| WO | WO 00/09084 | 2/2000 |
| WO | WO 00/10541 | 3/2000 |
| WO | WO 00/12278 | 3/2000 |
| WO | WO 00/13668 | 3/2000 |
| WO | WO 00/30617 | 6/2000 |
| WO | WO 00/66256 | 11/2000 |
| WO | WO 00/76673 | 12/2000 |
| WO | WO 01/03673 | 1/2001 |
| WO | WO 01/03821 | 1/2001 |
| WO | WO 01/13885 | 3/2001 |
| WO | WO 01/15664 | 3/2001 |
| WO | WO 01/45731 | 6/2001 |
| WO | WO 01/64188 | 9/2001 |
| WO | WO 01/87278 | 11/2001 |
| WO | WO 02/09669 | 2/2002 |
| WO | WO 02/15880 | 2/2002 |
| WO | WO 02/32462 | 4/2002 |
| WO | WO 02/38127 | 5/2002 |
| WO | WO 02/058674 | 8/2002 |
| WO | WO 02/78675 | 10/2002 |
| WO | WO 03/00202 | 1/2003 |
| WO | WO 03/008082 | 1/2003 |
| WO | WO 04/098561 | 11/2004 |

OTHER PUBLICATIONS

Barj et al., "Submicronic MgAl2O4 Powder Synthesis in Supercritical Ethanol", J. of Materials Sci., vol. 27, No. 8, pp. 2187-2192, (1992).
Bjork et al., "Degradable Starch Microspheres as a Nasal Delivery System for Insulin", International Journal of Pharmaceutics, vol. 47, pp. 233-238, (1988).
Bloch et al., "Dispersions of Hydrochlorothiazide and Chlorhalidone in Pentaerythritol", Pharm. Acta Helv., 58(1): pp. 14-22, (1983).
Bodmeier et al., "Polymeric Microspheres Prepared by Spraying Into Compressed Carbon Dioxide", Pharmaceutical Research, vol. 12, No. 8, pp. 1211-1217 (1995).
Bohnet "Calculation and Design of Gas/Solid-Injectors", Powder Tech, pp. 302-313, (1984).
Budrik et al., "Ejector Feeders for Pneumatic Transport Systems", Chemical Petroleum Engineering, vol. 14, Nos. 9-10, pp. 9-10, (Sep.-Oct. 1978).
Byron et al., "Drug Delivery Via the Respiratory Tract", Journal of Aerosol Medicine, vol. 7, No. 1, pp. 49-75, (1994).
Carpenter et al., "Modes of Stabilization of a Protein by Organic Solutes During Desiccation", Cryobiology, vol. 25, pp. 459-470, (1988).
Chang et al., "Precipitation of Microsize Organic Particles from Supercritical Fluids", AIChE Journal vol. 35, No. 11, pp. 1876-1882 (Nov. 1989).
Chien et al., "Intranasal Drug Delivery for Systemic Medications", Critical Reviews in Therapeutic Drug Carriers Systems, vol. 4, Issue 2, pp. 67-92, (1 Page), (1987).
Colthorpe et al., "The pharmacokinetics of pulmonary-delivered insulin: a comparison of intratracheal and aerosol administration to the rabbit", Pharmaceutical Research, vol. 9, No. 6, pp. 764-768. (1 page), (1992).
Dixon et al., "Polymeric Materials Formed by Precipitation with a Compressed Fluid Antisolvent", AIChE J., vol. 39, No. O, pp. 127-139, (1993).

Duchateau et al., "Bile Salts and Intranasal Drug Absorption", International Journal of Pharmaceutics, vol. 31, pp. 193-199, (1986).
Elliott et al., "Parenteral Absorption of Insulin From the Lung in Diabetic Children", Aust. Paediatr. J., vol. 23, pp. 293-297, (1987).
Fox et al., "Performance of a Venturi Eductor as a Feeder in a Pneumatic Conveying System", Powder & Bulk Engineering, pp. 33-36, (Mar. 1988).
Friedman., "Progress Toward Human Gene Therapy", Science, vol. 244, pp. 1275-1281, (Jun. 16, 1989).
Gansslen, "Uber Inhalation Von Insulin", Klin. Wochenschr., vol. 4, p. 71 with translation included (3 pages), (Jan. 1925).
Ghaderi et al., "A New Method for Preparing Biodegradable Microparticles and Entrapment of Hydrocortisone in DL-PLG Microparticles Using Supercritical Fluids", European J. of Pharm. Sci., vol. 10, No. 1, pp. 1-9, (Mar. 2000).
Govinda, "Aerosol Insulin Inhalation Enquiry" Indian J. Physiol. Pharmacol, vol. 3, pp. 161-167, (1959).
Habener, "Parathyroid Hormone: Secretion and Metabolism In Vivo", Proc. Nat. Acad. Sci. USA. vol. 68, No. 12, pp. 2986-2991, (Dec. 1971).
Hastings et al., "Clearance of Different-Sized Proteins from the Alveolar Space in Humans and Rabbits", J. Appl. Physiol., vol. 73, pp. 1310-1316. (1 page), (1992).
He et al., "Chitosan Microspheres Prepared by Spray Drying", International J. of Pharm. (Amsterdam), vol. 187, No. 1, pp. 53-65, (1999).
Hesch, "Pulsatile secretion of parathyroid hormone and its action on a type I and type II PTH receptor: a hypothesis for understanding osteoporosis", Calcified Tissue Int. vol. 42, pp. 341-344, (1988).
Hino et al., "Development of a new type nozzle and spray-drier for industrial production of fine powders", European J. of Pharmaceutics and Biopharmaceutics, vol. 49, pp. 79-85, (2000).
Hubbard et al., "Abstract Strategies for aerosol therapy of alpha 1-antitrypsin deficiency by the aerosol route", Lung. vol. 168, Supplement: 1990, Proceedings of the 8th Congress of SEP. Edited by H. Matthys, pp. 565-578, (1990).
Jung et al., "Particle Design Using Supercritical Fluids: Literature and Patent Survey", J. of Supercritical Fluids vol. 20, pp. 179-219, (2001).
Kohler et al., "Nicht Radioaktives Verfahren Zur Messung Der Lung'enpermeabilitat: Inhalation Von Insulin", Atemu. Lunaenkrkh. Jahraana., vol. 13, No. 5, pp. 230-232, (1987). For English Abstract see Schluter Reference.
Kovacs et al., "Hydroxyethylcellulose for Tablet Coating", Drug Dev. Ind. Pharm., vol. 16, pp. 2302-2323, (1990).
Laube et al., "Preliminary study of the efficacy of insulin aerosol delivered by oral inhalation in diabetic patients", JAMA. vol. 269, No. 16. pp. 2106-2109, (1 page), (Apr. 28, 1993).
Lee et al., "Development of an aerosol dosage form containing insulin", Journal of Pharmaceutical Sciences, vol. 65, No. 4, pp. 567-572, (1 page), (Apr. 1976).
Lehman, "Coating of Tablets and Small Particles with Acrylic Resins by Fluid Bed Technology", Int. J. Pharm. Tech. Prod. Mfr., 2(4), pp. 3143, (1981).
Liu et al., "Pulmonary Delivery of Free and Liposomal Insulin", Pharmaceutical Research, vol. 10, No. 2, pp. 228-232, (1993).
Masters, "The Process Stages of Spray Drying: Atomization", Spray Drying Handbook, pp. 230-247, (1979).
Meyer et al., "Preparation and in vitro characterization of gentamycin-impregnated biodegradable beads suitable for treatment of osteomyelitis", J. of Pharm. Sci., vol. 87, No. 9, p. 1149-1154, (Sep. 1, 1998).
Moneghini et al., "Processing of Carbamazepine-PEG 4000 Solid Dispersions with Supercritical Carbon Dioxide", International J. of Pharm., Netherlands, vol. 222, No. 1. pp. 129-138, (Jul. 3, 2001).
Mumenthaler et al., "Feasibility Study on Spray-Drying Protein Pharmaceuticals; Recombinant Human Growth Hormone and Tissue-Type Plasminogen activator", Pharm Res., 11(1), pp. 12-20, (1994).
Nagai et al., "Powder Dosage Form of Insulin for Nasal Administration", Journal of Controlled Release, vol. 1, pp. 15-22, (1984).

(56) References Cited

OTHER PUBLICATIONS

Neer et al., "The Use of Parathyroid Hormone Plus 1,25-Dihydroxyvitamin D to Increase Trabecular Bone in Osteoporotic Men and Postmenopausal Women", Osteoporosis, vol. 53, pp. 829-835, (1987).
Nieminen et al., "Aerosol Deposition in Automatic Dosimeter Nebulization", Eur. J. Resir. Dis. vol. 71, pp. 145-152, (1 page), (1987).
Patton et al, "(D) Routes of Delivery: Case Studies-(2) Pulmonary Delivery of Peptides and Proteins for Systemic Action", Advanced Drug Delivery Reviews, vol. 8, pp. 179-196, (1992).
Phillips et al, "Rapid Expansion from Supercritical Solutions: Application to Pharmaceutical Processes", International J. of Pharmaceutics, vol. 94, pp. 1-10 (1993).
Pikal et al., "Moisture Transfer From Stopper to Product and Resulting Stability Implications", Developments in Biological Standardization, vol. 74, International Symposium on Biological Product Freeze-Drying and Formulation, pp. 1, (1991).
Pikal, "Polymorphisms in Pharmaceutical Solids", AAPS, Annual Meeting and Expositions, San Antonio, TX, 2 pages, (Nov. 5, 1992).
Pittman et al., "Pneumatic Conveying of Bulk Solids Using a Vacuum Aerated Feed Nozzle", Solid Handling Conference Paper C4, Thames Polytechnic London, United Kingdom, pp. C41-CS1, (Jun. 10-12, 1986).
Rosenfeld et al., "Adenovirus-Mediated Transfer of a Recombinant a- 1-Antitrypsin Gene to the Lung Epithelium in Vivo", Science, vol. 252, pp. 431-434, (Apr. 19, 1991).
Ryden et al., "Effect of Polymers and Microspheres on the Nasal Absorption of Insulin in Rats", International Journal of Pharmaceutics, vol. 83, pp. 1-10, (1992).
Sajeev et al., "Oral controlled release formulation of diclofenac sodium by microencapsulation with ethyl cellulose", J. Microencapsulation, 19(6):753-760, (2002).
Sakr, "A New Approach for Insulin Delivery Via the Pulmonary Route: Design and Pharmacokinetics in Non-Diabetic Rabbits", International Journal of Pharmaceutics, vol. 86, pp. 1-7, (1 page), (1992).
Sanchez et al., "Development of Biodegradable Microspheres and Nanospheres for the Controlled Release of Cyclosporin A", International J. of Pharmaceutics, vol. 99, pp. 263-273, (1993).
Schluter et al., "Pulmonary Administration of Human Insulin in Volunteers and Type 1-Diabetics", Abstract Reproduction Form for Annual Meeting Program Published in Diabetes, one page, (Feb. 1, 1984).
Stribling et al., "The Mouse as a Model for Cationic Liposome-Based Aerosolized Gene Delivery", Journal of Biopharmaceutical Sciences, 3(1/2), pp. 255-263, (1992).
Tom et al., "Particle Formation with Supercritical Fluids—A Review", J. Aerosol. Sci., 22(5):555-584, (1991).
Tom et al., "Formation of Bioerodible Polymeric Microspheres and Microparticles by Rapid Expansion of Supercritical Solutions", Biotechnol. Prog., vol. 7, pp. 403-411, (1991).
Underwood et al., "A Novel Technique for the Administration of Bronchodilator Drugs Formulated as Dry Powders to the Anaesthetized Guinea Pig", Journal of Pharmacological Methods, vol. 26, pp. 203-210, (1991).
Wigley et al., "Insulin Across Respiratory Mucosae by Aerosol Delivery", Diabetes, vol. 20, No. 8, pp. 552-556, (1 page), (1971).
Witham, "Dry Dispersion With Sonic Velocity Nozzles", Workshop on Dissemination Techniques for Smoke and Obscurants Chemical Systems Laboratory, Aberdeen Proving Group, MD, pp. 1-26, (Mar. 14-16, 1983).
Yoshida, "Absorption of Insulin Delivered to Rabbit Trachea Using Aerosol Dosage Form", Journal of Pharmaceutical Sciences, vol. 68, No. 5, pp. 670-671, (1 page), (May 1979).
Zholob et al., "Effect of Injector Unit Design on the Particle Size of Atomized Powder", 0038-5735/79/1806, Plenum Publishing Corporation, pp. 362-364, Dnepropetrovsk State University, Translated from Poroshkovava Metalluraiva, (1979).
EP Search Report for Application No. 97926420.7 (NEKT/0013) dated Dec. 16, 2005.
Partial EP Search Report for Application No. 97926420.7 (NEKT/0013) dated Jan. 4, 2006.
EPO Communication for European Application No. 97926420.7. (NEKT/0013EP) dated Nov. 2, 2006.

* cited by examiner

PARTICULATE MATERIALS

CROSS-REFERENCE TO RELATED APPLICATIONS

This application is a continuation of U.S. patent application Ser. No. 15/098,183, filed on Apr. 13, 2016, now U.S. Pat. No. 9,700,529, which is a continuation of U.S. patent application Ser. No. 13/622,272, filed on Sep. 18, 2012, now U.S. Pat. No. 9,339,459, which is a continuation of U.S. patent application Ser. No. 10/422,342, filed on Apr. 24, 2003, now U.S. Pat. No. 8,273,330, which claims priority to GB 0216562.9, filed Jul. 17, 2002, to GB 0211086.4, filed May 15, 2002, to GB 0210268.9, filed May 7, 2002, and to GB 0210174.9, filed May 3, 2002, all of which are incorporated by reference herein in their entireties.

BACKGROUND OF THE INVENTION

Field of the Invention

The present invention relates to active substances in particulate form, to methods for preparing them and to their uses.

Certain pharmaceuticals may be delivered to the nose and/or lungs of a patient by inhalation, using an inhaler device of which there are several known types. Pulmonary delivery by aerosol inhalation has received much attention as an attractive alternative to intravenous, intramuscular, and subcutaneous injection, since this approach eliminates the necessity for injection syringes and needles. Pulmonary delivery also limits irritation to the skin and body mucosa which are common side effects of transdermally, iontophoretically and intranasally delivered drugs, eliminates the need for nasal and skin penetration enhancers (typical components of intranasal and transdermal systems often cause skin irritation/dermatitis), is economically attractive, is amenable to patient self-administration and is often preferred by patients over alternative modes of administration.

Of particular interest in the context of the present invention are pulmonary delivery techniques which rely on the inhalation of a pharmaceutical formulation by a patient so that the active drug within the dispersion can reach the distal (alveolar) regions of the lung.

A variety of aerosolization systems have been proposed to disperse pharmaceutical formulations. For example, U.S. Pat. Nos. 5,785,049 and 5,740,794, the disclosures of which are herein incorporated by reference, describe exemplary active powder dispersion devices which utilize a compressed gas to aerosolize a powder. Other types of aerosolization systems include metered dose inhalers (MDIs), which typically have a drug that is stored in a propellant, and nebulizers (which aerosolize liquids using a compressed gas, usually air).

An alternative type of inhaler is known as a dry powder inhaler (DPI) and delivers the drug (or a composition containing the drug, for instance together with a pharmaceutically acceptable excipient) in the form of a dry airborne particulate powder. DPIs include single use inhalers such as those disclosed in U.S. Pat. Nos. 4,069,819, 4,995,385, 3,991,761 and 6,230,707, and in WO-99/45986, WO-99/45987, WO-97/27892 and GB-1 122 284; multi-single dose inhalers such as those disclosed in U.S. Pat. Nos. 6,032,666 and 5,873,360 and in WO-97/25086; and multi-dose inhalers containing powder in a bulk powder reservoir such as those disclosed in U.S. Pat. No. 4,524,769.

Particulate active substances, such as drugs, may be produced by a variety of known methods, including for example crystallisation from solution, anti-solvent precipitation from solution, milling, micronisation, spray drying, freeze drying or combinations of such processes. Also known are particle formation processes which make use of supercritical or near-critical fluids, either as solvents for the substance of interest—as in the process known as RESS (Rapid Expansion of Supercritical Solution—see Tom & Debenedetti, *J. Aerosol. Sci.,* 22 (5), 555-584 (1991))—or as anti-solvents to cause the substance to precipitate from another solution—as in the process known as GAS (Gas Anti-Solvent) precipitation—see Gallagher et al, *ACS Symp. Ser.,* 406, p334 (1989).

In general, however, known processes for producing inhalable drugs can often yield particles which give less than satisfactory performance in DPI and similar delivery devices. For example, the dispersion of many prior art dry powder formulations from inhalation devices exhibits a flow rate dependence such that dispersion of the powder from the device increases with the patient's inspiratory effort. Alternatively, many formulations require mixing or blending with larger carrier particles such as lactose in order to deliver the particles effectively to the deep lung.

It would therefore be desirable to provide particulate drugs, and indeed other active substances which may need to be delivered as dry (ie, without a fluid carrier) powders using a DPI or analogous mechanism, which can demonstrate improved performance in such a context, in particular improved dispersibility and aerosol performance in fluids and especially in gases such as air.

SUMMARY OF THE INVENTION

The present invention provides particulate powders, such as might be of use for delivery using a DPI or similar delivery device, having properties which may be beneficial to the DPI delivery process. These properties are illustrated in the examples below.

In particular, according to a first aspect, the present invention can provide an active substance in particulate form, preferably prepared using a SEDS™ particle formation process as defined below, which exhibits one or more (preferably two or more, more preferably at least three) of the following characteristics:

a) the particles have a low surface energy. In particular, they preferably exhibit a low value for the surface energy related parameter $\gamma_S^D$ (the dispersive component of surface free energy, as defined in the examples below, which reflects non-polar surface interactions) and/or for the parameter $\Delta G_A$ (the specific component of surface free energy of adsorption, again as defined in the examples, which reflects polar surface interactions), for instance when compared to particles of the same active substance prepared using a non-SEDS™ particle formation process and preferably having the same or a smaller volume mean diameter. In the case of the parameter $\Delta G_A$, the value for the active substance of the present invention, for any given polar solvent, is preferably lower by a factor of at least 1.2, preferably at least 1.4 or 1.5, than that for the corresponding non-SEDS™-produced substance.

b) the particles exhibit a low surface adhesion and/or cohesiveness (which may be related to their surface energy). In particular, they may exhibit lower adhesiveness than those of the same active substance produced by a non-SEDS™ particle formation process.

c) the particles show little or no tendency for aggregation (again this may be related to their surface properties such as surface energy and adhesiveness), or at least form less stable aggregates than those of the same active substance produced by a non-SEDS™ particle formation process.

d) the particles have a volume mean aerodynamic diameter of 7 μm or less, preferably 5 μm or less, more preferably 4 μm or 3 μm or less, such as from 1 to 5 μm, from 1 to 4 μm or from 1 to 2 μm e) the particles have a volume mean geometric diameter of 5 μm or less, preferably 4 μm or less, more preferably from 1 to 5 μm, most preferably from 1 to 4 or from 2 to 4 μm.

f) the particles have a particle size distribution ($x_{90}$)of 10 μm or less, preferably also a value for ($x_{98}$) of 10 μm or less, preferably also a value for ($x_{99}$) of 10 μm or less. Typically each of these values will be from 0.5 to 10 μm.

g) when measured using a cascade impactor technique (at low turbulence), the particles have a particle size spread, defined as $(x_{90}-x_{10})/x_{50}$, of 1.3 or less, preferably of 1.25 or 1.2 or less, volume mean diameter of 6 μm or less, preferably of 5.5 μm or less, more preferably of 5.2 μm or less. Their particle size spread under these conditions is preferably at least 5%, more preferably at least 10%, still more preferably at least 12%, smaller than that of the same active substance produced by a non-SEDS™ particle formation process, and their volume mean diameter preferably at least 10%, more preferably at least 15%, still more preferably at least 20%, smaller than that of the non-SEDS™ substance.

h) the particles are crystalline, or substantially so, and in particular are more crystalline than those of the same active substance produced by a non-SEDS™ particle formation process. Their X-ray diffraction patterns thus preferably exhibit reduced diffraction line broadening and/or a higher signal-to-noise ratio than the X-ray diffraction patterns for the same active substance produced by a non-SEDS™ process. The crystalline particles may exhibit reduced crystal lattice imperfections such as strain defects (point defects and/or dislocations) and/or size effects (grains, small-angle boundaries and/or stacking faults), as compared to crystals of the same active substance produced by a non-SEDS™ process—such imperfections tend to be associated with increased line broadening in the X-ray diffraction patterns. In particular, the particles may exhibit a lower crystal strain, and/or a higher crystal domain size, than crystals of the same active substance produced by a non-SEDS™ particle formation process.

i) where the active substance is capable of existing in two or more different polymorphic forms, the particles consist of only one such form, with a purity of 99.5% w/w or greater, preferably of 99.8% w/w or greater, with respect to the other polymorphic forms. More preferably, the active substance has a higher activation energy for conversion to one or more other polymorphic forms than does a sample of the same active substance prepared using a non-SEDS™ particle formation process.

j) the particles have a lower surface charge (for instance, mean specific charge) than those of the same active substance produced by a non-SEDS™ particle formation process.

k) the particles exhibit superior powder flow properties (which may be related to lower surface charge and/or adhesiveness) as compared to those of the same active substance produced by a non-SEDS™ particle formation process; for instance, they may be more free-flowing and/or they may deaggregate more efficiently when dispersed in a fluid such as in a DPI device, particularly at low turbulence and/or shear stress levels.

l) the particles have a bulk powder density which is lower than that of the same active substance produced by a non-SEDS™ particle formation process. They preferably have a bulk powder density of less than 0.5 μg/cm$^3$, more preferably of 0.4 g/cm$^3$ or less, most preferably of 0.2 g/cm$^3$ or less.

m) the particles have a specific surface area which is higher than that of the same active substance produced by a non-SEDS™ particle formation process.

n) the "shape factor" of the particles, by which is meant the ratio of (a) their measured specific surface area (ie, surface area per unit volume) to (b) their theoretical specific surface area as calculated from their measured diameters assuming spherical particles, is higher than that of the same active substance produced by a non-SEDS™ particle formation process. Preferably this shape factor is at least 2, more preferably at least 3, most preferably at least 3.5.

o) the "shape coefficient", $\alpha_{S,V}$ of the particles, determined from image (eg, SEM) analysis and as defined in the following equation:

$$\alpha_{S,V} \cong 6 d_s^3 / d_v^3$$

where the mean projected diameter, $d_s$, is given by:

$$d_s = (4S/\pi)^{1/2} = ((2/\pi)(ab+bc+ca))^{1/2} \text{ and}$$

the volume particle diameter, $d_v$, is given by $$d_v = (6V/\pi)^{1/3} = (6abc/\pi)^{1/3}$$

is higher than that of the same active substance produced by a non-SEDS™ SEDS™ particle formation process, preferably at least 1.5 times as great, more preferably at least twice as great. Preferably this shape coefficient is at least 10, more preferably at least 15, most preferably at least 18 or at least 20. It may alternatively be calculated from specific surface area measurements, laser diffraction particle size measurements and the theoretical crystal density, as defined in the following equation:

$$S_v = \alpha_{S,V} / \rho_{x\ min} \int^{x\ max} x^{-1} q_3(x) dx$$

p) the "aerodynamic shape factor" of the particles, $\chi$, is greater than that for the same active substance produced by a non-SEDS™ particle formation process, preferably at least 20% greater, more preferably at least 30% or at least 40% greater $\chi$ is the ratio of the drag force on a particle to the drag force on the particle volume-equivalent sphere at the same velocity, and may be calculated as described in the following equation:

$$\chi \cong ((C_d(d_S) C_c(d_V)) / (C_d(d_V) C_c(d_S)))(d_S/d_V)^2$$

For a product according to the invention it may be 1.4 or greater, preferably 1.5 or greater, most preferably 1.7 or 1.8 or greater, q) the particles have reduced surface roughness compared to those of he same active substance produced by a non-SEDS™ particle formation process.

By "non-SEDS™ particle formation process" is meant a particle formation process other than the non-SEDS™ process defined below, for example one involving micronisation, granulation and/or solvent crystallisation under sub-critical conditions, and in particular one involving micronisation. In general, comparisons between substances according to the invention and those made by non-SEDS™ techniques are suitably made using in each case particles of

DETAILED DESCRIPTION

Figure 1:
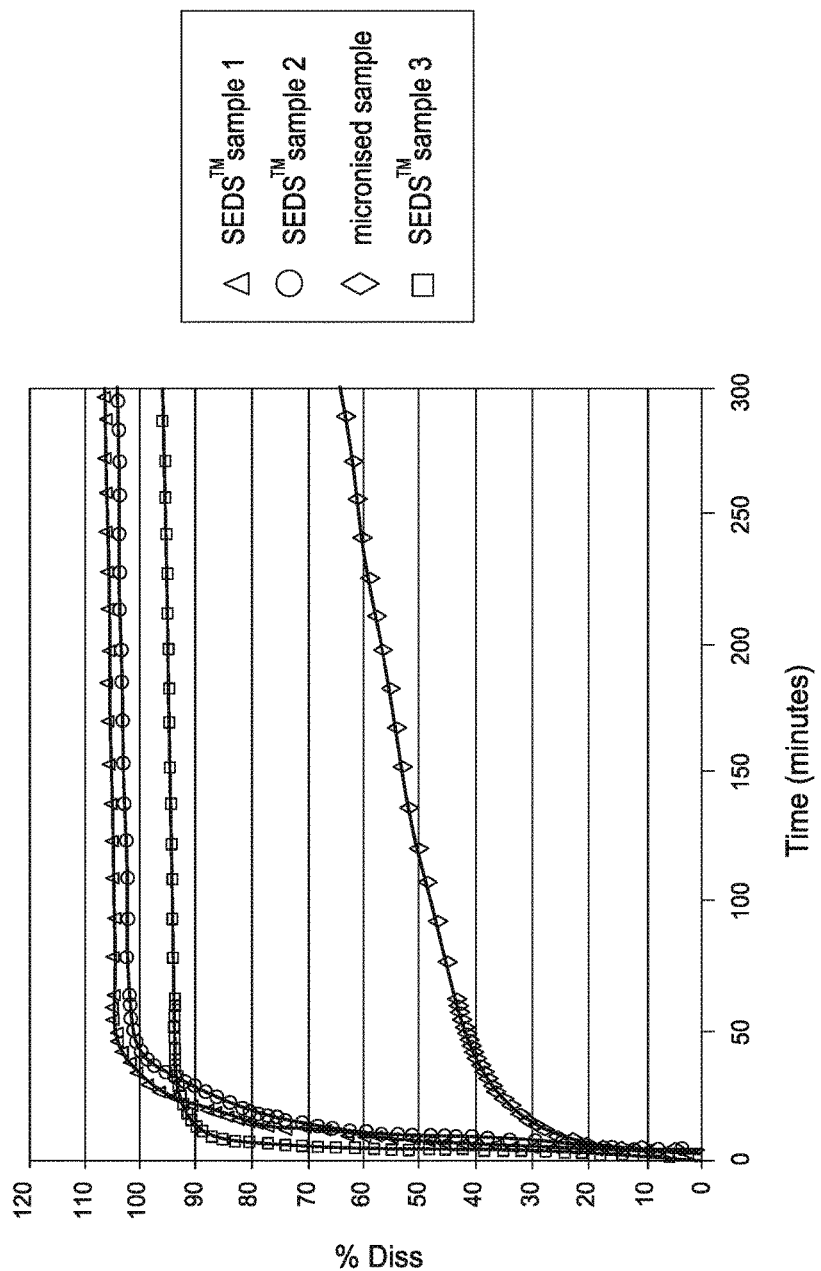
FIG. 1 depicts the percentage dissolution against time for particles processed according to the invention compared to micronised.

It has been found that particulate active substances having one or more of the above properties tend to exhibit improved performance, in particular good dispersibility, in delivery devices such as inhalers, especially dry powder inhalers and more especially passive dry powder inhalers. In particular a correlation has been found between lower particle surface energy and improved DPI performance. Similarly, lower strain, higher crystallinity and higher polymorphic purity have been associated with reduced agglomeration and particle adhesion, and with lower electrostatic charge, again properties which lead to improved DPI performance. Higher specific surface areas, and higher shape factors, have also been found to accompany improved DPI performance. For a given particle size, products according to the invention can demonstrate significantly better performance in passive dry powder inhalers than products made by conventional techniques such as spray drying, freeze drying, granulation and in particular micronisation.

Thus, the active substance of the invention, when used in a passive dry powder inhaler or analogous delivery device (for example the commercially available Clickhaler™), preferably yields a fine particle fraction in the emitted dose of 20% or greater, preferably 26% or greater, more preferably 31% or greater, in cases 35% or 40% or 50% or even 55% or greater. Instead or in addition, its fine particle fraction may be at least 20% greater, preferably at least 25% or 30% or 40% or 50% or 60% or 80% or 100% greater, more preferably at least 110% or 120% or 130% or 140% greater, than that of the same active substance produced by a non-SEDS™ particle formation process and having the same or a smaller volume mean diameter.

The active substance is preferably in a substantially (eg, 95% w/w, preferably 98% or 99% w/w or greater) pure form. It preferably contains low levels of residual solvent, for example less than 500 ppm, more preferably less than 200 ppm, most preferably less than 150 or 100 ppm residual solvent, by which is meant solvent(s) which were present at the point of particle formation. Still more preferably the substance contains no detectable residual solvent, or at least only levels below the relevant quantification limit(s). In particular residual solvent levels in the bulk particles, as opposed to merely at their surfaces, are likely to be lower than in particles of the same active substance produced by a non-SEDS™ process.

In cases, the fine particle fraction yielded by an active substance according to the invention, for instance in an Andersen™ cascade impactor, may be up to 150% or 175% or even 200% or 250% or 280% of that of the same active substance produced by a non-SEDS™ process. Such improvements may often be exhibited even if the particle size of the substance of the invention is significantly greater (eg, at least 30% or 50% or 75% or 90% greater) than that of the non-SEDS™-produced substance. They can also be exhibited in the absence of dispersion enhancing additives such as surfactants, in the absence of excipient/carrier materials and/or in unimodal (with respect to particle size) systems.

Particular improvements (with respect to substances made by non-SEDS™ processes) may be seen where the active substance is used alone as opposed to in a blend with an excipient such as lactose.

The total emitted dose for a substance according to the invention may also, in this context, be at least 10% greater, preferably at least 15% greater, more preferably at least 20% or 25% or 30% greater, than that for the same active substance made by a non-SEDS™ process, either with or without excipient(s). Generally the substances of the invention may deposit on the impactor stages with a narrower distribution (typically weighted more to the lower stages such as 1 to 3) than for those made by non-SEDS™ processes.

At relatively low dispersing pressures, for instance 2 bar or less, an active substance according to the invention has been found capable of yielding a significantly higher proportion of primary particles in the respirable size range than the same active substance produced by a non-SEDS™ process, the latter often tending to form stable (ie, not dispersible at these pressures) agglomerates above the preferred 5 μm limit. This again indicates reduced particle cohesiveness and/or reduced inter-particulate contact area in an active substance according to the invention. The volume mean particle diameter $d_{4,3}$ of the particles of the invention (calculated from cascade impactor data) may thus appear larger than that for non-SEDS™-produced particles when dispersed at pressures of 2 bar and above, but smaller at pressures below 2 bar, for instance 1.8 bar or below, where the dispersion (or deaggregation) ability of the particles plays a more dominant role.

Since the viscous shear stress within the impactor will affect the dispersion behaviour of the particles and hence their apparent volume mean diameter, particles according to the invention exhibit volume mean diameters lower than those of their non-SEDS™ SEDS™ equivalents at lower viscous shear stresses, for instance below 20 $Nm^{-2}$ or even up to 30 or 40 $Nm^{-2}$.

At such low shear stress levels, particles according to the invention appear to undergo significantly less aggregation, or to form significantly less stable aggregates, than those produced by a non-SEDS™ process which may produce stable aggregates well outside the 5 μm respirable limit. The particles of the invention, at these shear stress levels (or at least at shear stress levels between 5 and 30 $Nm^{-2}$ or between 10 and 30 $Nm^{-2}$) can produce a large fraction of primary particles in the respiratory size range, preferably having a volume mean diameter of less than 6 or more preferably less than 5 μm.

Thus, the volume mean particle diameter of an active substance according to the invention, derived from cascade impactor data in the manner defined in the Examples below, may be at least 10% smaller, preferably at least 15% or at least 20% smaller, than that of the same active substance produced by a non-SEDS™ particle formation technique, even where its volume mean diameter measured at higher dispersions using another technique such as laser diffraction or time-of-flight is greater than (for instance, up to 30% or 50% or even 100% greater than) that of the non-SEDS™ substance. This indicates that for a given size, particles according to the invention can give superior performance on aerosolisation.

Accordingly, particulate active substances of the present invention may be particularly advantageous for use with passive dry powder inhalers which operate in the lower region of turbulent stresses when dispersing the powder they contain.

In the context of the present invention, a passive dry powder inhaler is a device for use in delivering a powdered active substance to a patient, in which the patient's inspiratory effort is used as the sole powder dispersing means. In other words, the powder is not delivered in a pressurised fluid as in many metered dose inhalers, and nor does its delivery require the use of a rotating impeller or other mechanical means.

A second aspect of the present invention provides a method for selecting a particulate active substance for use in a dry powder inhaler, in particular a passive dry powder inhaler, which method involves the assessment of, and selection on the basis of, one or more (preferably two or more, more preferably three or more) of the above described properties of active substances according to the first aspect of the invention.

A third aspect provides the use of an active substance according to the first aspect, in a dry powder inhaler and in particular in a passive dry powder inhaler, for the purpose of achieving improved active substance delivery. Improved delivery in this context may involve improved powder dispersion, more accurate dosage delivery, more consistent dosage delivery and/or a higher fine particle fraction in the emitted dose, in particular at relatively low dispersing pressures such as 2 bar or less or 1.8 bar or less.

Particle surface energies may be measured using inverse gas chromatography (IGC), for instance using a gas chromatograph from the Hewlett Packard™ series. Surface energy measurements ideally take account of the dispersive component of the surface free energy, $\gamma_S^D$, the specific component of the surface free energy of adsorption, $\Delta G_A$, the acid-base parameters and/or the total (Hildebrand) solubility parameter, which takes into account dispersive, polar and hydrogen-bonding interactions on particle surfaces and thus reflects the inter-particle adhesion. The dispersive component may be assessed using non-polar probes such as alkanes, and the specific component $\Delta G_A$ may be assessed using data from both polar and non-polar probes, the former having both dispersive and specific components of surface free energy of adsorption.

Thus, gas chromatography measurements suitably involve the use of both non-polar and polar probes, examples of the former being alkanes such as pentane, hexane, heptane, octane and nonane and of the latter being diethyl ether, toluene, acetone, ethyl acetate, chloroform, dioxane, dichloromethane and tetrahydrofuran.

In the case of the dispersive component $\gamma_S^D$, the value for the active substance of the present invention is preferably at least 5% lower, more preferably at least 10% lower, most preferably at least 12% or 15% or 20% or 30% lower, than that for the same active substance made by a non-SEDS™ particle formation process.

In the case of the specific component $\Delta G_A$, the value for the active substance of the present invention is preferably at least 10% lower, more preferably at least 15% lower, most preferably at least 20% or 30% or 50% or 80% lower, than that for the same active substance made by a non-SEDS™ particle formation process.

In the case of the Hildebrand solubility parameter δ, the value for the active substance of the present invention is preferably at least 5% lower, more preferably at least 8% lower, most preferably at least 10% lower, than that for the same active substance made by a non-SEDS™ particle formation process.

Overall, particulate active substances according to the present invention tend to have lower surface activity (for example with respect to solvent adsorption) and greater surface stability than those produced by non-SEDS™ particle formation processes, with a more ordered surface structure. Their lower surface energy may be manifested by a lower value for $K_A$ and/or $K_D$, for instance as measured in Example 2, indicative of weaker acidic and/or basic interactions respectively at the particle surfaces. For instance, their $K_A$ may be at least 5%, preferably at least 10% or at least 12%, lower than that of the same active substance made by a non-SEDS™ particle formation process, and/or their $K_D$ may be at least 30%, preferably at least 50% or at least 60% lower.

The specific surface energy $E_S$ of a particulate active substance according to the invention, calculated as per the following equation:

$$E_s = 0.683(\delta^2/\alpha_{S,V}^{2/3})\Omega^{1/3}$$

where δ is the Hildebrand solubility parameter, $\alpha_{S,V}$ is the shape coefficient, and Ω is the molecular volume is preferably at least 10%, more preferably at least 20%, still more preferably at least 30% or 40%, lower than that of the same active substance produced by a non-SEDS™ particle formation process, and might typically be 100 mJ/m² or lower, more preferably 90 or 80 or 70 mJ/m² or lower.

A lower aggregation tendency in particles according to the invention may be reflected in a lower theoretical aggregate tensile strength σ, which may be calculated as described in the following equation:

$$\sigma \cong 15.6(\rho_B/\rho_C)^4 W/d_s$$

where $\rho_B$ and $\rho_C$ are the bulk density and particle crystal density, respectively, and W is the work of adhesion. Preferably the ratio of σ for particles of the invention to that for particles of the same active substance produced by a non-SEDS™ process is 0.8 or lower, more preferably 0.5 or lower, most preferably 0.3 or 0.2 or 0.1 or lower, especially when polar interactions are taken into account.

Similarly, the aerodynamic stress required to disperse aggregates of particles according to the invention (for instance, calculated from cascade impactor measurements, as described in the Examples below) is typically lower than that required to disperse aggregates of the same active substance prepared by a non-SEDS™ particle formation process. Ideally the ratio of the two stresses (SEDS™ product: non-SEDS™ product) is 0.8 or lower, more preferably 0.5 or lower, most preferably 0.3 or 0.2 or lower. Inter-particle aggregation can be particularly relevant to DPI performance since such aggregates tend to survive the pre-separation stage. Aggregation tendencies can also be relevant when an active substance is blended with a carrier such as lactose, where dispersion may depend on the break-up of active-carrier aggregates—again, typically, substances according to the invention may tend to form less stable aggregates with carrier particles.

Particle sizes may be measured for instance using (a) an AeroSizer™ time-of-flight instrument (which gives a mass mean aerodynamic equivalent particle diameter, MMAD, measured at Reynolds numbers greater than 1) or (b) a laser diffraction sensor such as the Helos™ system (which provides a geometric projection equivalent mass median diameter). Volume mean aerodynamic and geometric diameters respectively may be obtained from these measurements using commercially available software packages.

The aerodynamic diameter $d_A$ of a particulate active substance according to the invention, measured according to the examples below, is preferably 2 μm or below, more preferably 1.8 μm or below, most preferably 1.6 μm or below.

Particle size distributions may be measured using laser diffraction and/or time-of-flight measurements, for instance using an AeroSizer™ time-of-flight instrument equipped with an AeroDisperser™ (TSI Inc, Minneapolis, USA) and/or a Helos™ laser diffraction sensor with Rodos™ dry powder air dispersion system (Sympatec GmbH, Germany). Volume particle size distributions based on aerodynamic equivalent particle diameters are preferred. Ideally time-of-flight measurements are gathered at high shear forces, high deaggregation levels and/or low feed rates, in order to facilitate production of primary aerosol particles.

Particle size distribution (PSD) data, in particular obtained by laser diffraction measurements, may also be used to calculate the shape coefficient $\alpha_{S,V}$ of particles in the manner described above.

An active substance according to the invention will suitably have a cumulative particle size distribution such that more than 98% of the particles are within the respirable particle size range from 0.5 to 10 μm.

Scanning electron microscopy (SEM) may also be used to measure characteristic particle dimensions and thus characteristics such as particle aspect ratios and shape factors.

Crystallinity of a particulate material may be determined using X-ray powder diffraction, preferably high resolution X-ray powder diffraction such as using a synchrotron radiation source. Using commercially available software, X-ray diffraction data may be employed to assess the distribution of crystalline domain sizes and the degree of strain in the crystals.

X-ray diffraction line broadening can provide an indication of crystal lattice imperfections such as strain defects (point defects or dislocations) and size effects (grains, small-angle boundaries or stacking faults). Line broadening may be manifested for instance by an increased peak width (eg, full width at half maximum height, FWHM) and/or an increased integral breadth β* (the width of rectangle having the same area A and height I as the observed line profile, ie, β*=A/I), for one or more of the diffraction peaks.

Preferably, for at least one peak in its X-ray diffraction pattern (ideally for two or more, even three or more, peaks), the active substance of the invention exhibits a FWHM which is at least 20% lower, more preferably at least 25% lower, most preferably at least 30% or 40% or 50% lower, than that of the corresponding peak (ie, the peak for the same crystal plane) in the X-ray diffraction pattern of the same substance produced by a non-SEDS™ particle formation process. The FWHM of at least one, ideally of at least two or three or even of all, peaks is preferably 0.1° or less, more preferably 0.09°, or less, most preferably 0.08° or less.

For at least one peak in its X-ray diffraction pattern (ideally for two or more, even three or more, peaks), the active substance of the invention preferably exhibits an integral breadth β* which is at least 20% lower, more preferably at least 25% lower, most preferably at least 30% or 40% or 45% lower, than that of the corresponding peak in the X-ray diffraction pattern of the same substance produced by a non-SEDS™ particle formation process. The integral breadth of at least one, ideally of at least two or three or even of all, peaks is preferably 0.11° or less, more preferably 0.1° or less.

A reduced level of crystal lattice imperfections, in a particulate product according to the invention, may also be manifested by a shift in position, towards higher 2θ values (typically a shift of 0.0005°, or more, such as of from 0.0005 to 0.005 or from 0.001 to 0.0030°, of one or more of the diffraction peaks. This may be associated with a decrease in crystal d-spacing (Δd/d) of 0.5% or more, typically 1% or more, such as from 1 to 2%, in the product of the invention, and with a corresponding reduction in crystal volume, ΔV/V, of 0.5% or more, typically 1% or more, such as from 1 to 2%.

Levels of crystal lattice imperfections may also be assessed with reference to the crystal domain sizes and/or the crystal strain. Domain sizes are typically significantly greater for products according to the invention, compared to the same active substance produced using a non-SEDS™ particle formation process, and crystal strain is typically significantly lower. Such parameters may be calculated from X-ray diffraction patterns, for instance by analysing the diffraction peak profiles as a convolution of Cauchy and Gauss integral breadths containing size and strain (distortion) contributions, as known in the art, This allows calculation of for example surface-weighted ($D_V$) and/or volume weighted ($D_S$) domain sizes, and of a mean-square (Gaussian) strain, ε, which is the total strain averaged over infinite distance.

Preferably, the active substance of the invention exhibits a surface-weighted domain size $D_S$ which is at least 15% higher, more preferably at least 20% higher, most preferably at least 30% or 35% higher, than that of the same substance produced by a non-SEDS™ particle formation process. It preferably exhibits a volume-weighted domain size $D_V$ which is at least 10% higher, more preferably at least 15% higher, most preferably at least 20% or 25% higher, than that of the same substance produced by a non-SEDS™ particle formation process. $D_S$ may for example be 400 Å or greater, and $D_V$ may be 700 Å or greater, in an active substance according to the invention.

Preferably the active substance of the invention exhibits a total strain ε which is at least 30% lower, more preferably at least 35% lower, most preferably at least 40% or 45% lower, than that of the same substance produced by a non-SEDS™ particle formation process. Its total strain may for instance be $0.7\times10^{-3}$ or lower, preferably $0.6\times10^{-3}$ or lower, most preferably $0.5\times10^{-3}$ or lower.

Domain size and strain may alternatively be calculated from the X-ray diffraction data by Le Bail diffraction profile fitting. Using such computational methods, an active substance according to the invention preferably exhibits a volume-weighted domain size which is at least 50% higher, more preferably at least 80% higher, most preferably at least 90% higher, than that of the same substance produced by a non-SEDS™ particle formation process. It preferably exhibits a strain which is at least 40% lower, more preferably at least 50% lower, most preferably at least 60% lower, than that of the same substance produced by a non-SEDS™ particle formation process.

An active substance according to the invention may have an amorphous content of less than 5% w/w, preferably less than 2% w/w, more preferably less than 1 or even than 0.5 or 0.2% w/w. Ideally its amorphous phase content is at least 10 times, preferably at least 20 or even 40 or 50 times, lower than that of the same active substance produced by a non-SEDS™ particle formation process.

A higher bulk crystallinity, in an active substance according to the invention, may be manifested by a lower moisture uptake at any given temperature and humidity, and/or by a thermal activity profile with no exothermic or endothermic peaks, for instance as measured in the examples below.

Polymorphic purity may be assessed for instance using melting point data (eg, differential scanning calorimetry) or more preferably using X-ray powder diffraction (for instance the small-angle X-ray scattering (SAXS) technique) to detect polymorphic transitions during heating, based on the diffraction peaks characteristic of the polymorphs.

An active substance according to the invention is preferably more stable, with respect to polymorphic transitions, than a sample of the same active substance prepared using a non-SEDS™ particle formation process; it will thus typically have a higher activation energy for conversion to one or more other polymorphic forms than will the non-SEDS™ sample for the same polymorphic transition. More preferably, when heated at a rate of 10° C. per minute or greater at atmospheric pressure, the active substance of the invention will not alter its polymorphic form. Instead or in addition, the time required for formation of one or more other polymorphs of the active substance, calculated for instance from X-ray diffraction and thermal analysis data, is preferably 80 seconds or greater, more preferably 90 seconds or greater. The active substance preferably contains no detectable seed nuclei of polymorphic forms other than that desired to be present.

Enhanced crystallinity and/or polymorphic purity in active substances according to the invention are believed to contribute to an overall higher physical stability as compared to the same active substances prepared using non-SEDS™ particle formation techniques.

Surface electric charge may be assessed as specific charge. The electrostatic charge carried by a particulate material may be measured for instance in a Faraday well. Alternatively the particulate material may for instance be subjected to triboelectrification by agitating it against an electrically conductive contact surface, for example in a turbula mixer or cyclone separator, and its charge and mass determined both before and after triboelectrification, suitably using an electrometer, to give a value for specific charge. This process may also be used to give a measure of the adhesion properties of the particles, by measuring the mass of the original sample and that removable from the mixer/separator in which it was agitated and calculating the weight percentage of the sample lost by adhesion to the contact surface(s) of the vessel.

Adhesion may also be assessed using a simple test of the type described in Examples 3 below, in which a sample is agitated in a container, and the non-adhering material then removed from the container and weighed, to allow calculation of the percentage of the original sample adhering to the container surfaces, By way of example, an active substance according to the invention preferably has a mean specific charge of from −5 to +5 $nCg^{-1}$, more preferably from −1 to +1 $nCg^{-1}$, and/or a mean specific charge which is at least 50%, preferably at least 70%, most preferably at least 80% or 90% or 95%, lower than that of the same active substance produced by a non-SEDS™ particle formation process.

Following triboelectrification using a Turbula™ mixer, an active substance according to the invention preferably has a mean specific charge which is at least 30% lower, more preferably at least 50% lower, most preferably at least 75% or 80% or 90% or 95% lower, than that of the same active substance produced by a non-SEDS™ process. Following triboelectrification using a cyclone separator, an active substance according to the invention preferably has a mean specific charge which is at least 30% lower, more preferably at least 50% lower, most preferably at least 75% or 80% or 85% lower, than that of the same active substance produced by a non-SEDS™ process.

The mean adhesion fraction (ie, the fraction of adhered material) assessed in the manner described above following triboelectrification in a turbula mixer, is preferably 20% w/w or less, more preferably 10% w/w or less, most preferably 5% or 2% w/w or less, for an active substance according to the invention. It is preferably at least 50% lower, more preferably at least 75% lower, most preferably at least 80% or 90% lower, for an active substance according to the invention than for the same active substance produced by a non-SEDS™ process.

The mean adhesion fraction, assessed in the manner described above following triboelectrification in a cyclone separator, is preferably 20% w/w or less, more preferably 10% w/w or less, most preferably 5% w/w or less, for an active substance according to the invention. It is preferably at least 40% lower, more preferably at least 50% lower, most preferably at least 60% or 65% lower, for an active substance according to the invention than for the same active substance produced by a non-SEDS™ process.

In cases, an active substance produced by a non-SEDS™ process may exhibit at least 5 times as much adhesion as the same active substance produced by a SEDS™ process, preferably at least 8 times or at least 10 times or at least 15 times that of the SEDS™ substance.

The adhesion force per unit area to a highly oriented pyrolytic graphite substrate assessed using atomic force microscopy in the manner described above is preferably less than 60% of, more preferably less than 30% of, most preferably less than 15% of that for particles of the same active substance produced by a non-SEDS™ process.

Powder flow properties may be assessed by analysing the dynamic avalanching behaviour of a particulate product, such as using an Aeroflow™ powder avalanching apparatus (Amherst Process Instruments, Amherst, USA), for instance as described in the Examples below.

Superior powder flow properties, in an active substance according to the invention, may be manifested by a strange attractor plot which is closer to the origin and/or has a smaller spread than that for the same active substance produced by a non-SEDS™ process. A strange attractor plot may be obtained, again as described in the examples below, from powder avalanching data (in particular, time intervals between avalanches) using the method of Kaye et al, Part. Charact., 12 (1995), 197-201. Substances according to the invention tend to exhibit lower mean avalanche times (for example at least 5% or even 8% lower at 100 s/rev, at least 10% or even 14% lower at 145 s/rev) than corresponding products of non-SEDS™ processes. They may show a lower irregularity of flow (for example at least 5% or even 8% lower at 100 s/rev, at least 8% or even 10% lower at 145 s/rev) than corresponding non-SEDS™ products, irregularity of flow being assessed in terms of avalanche scatter.

The bulk powder density of an active substance according to the invention may be measured in conventional manner, for example using a volumetric cylinder, and is preferably at least 20% lower, more preferably at least 50% lower, most preferably at least 60% or 70% or 80% lower, than that of the same active substance produced by a non-SEDS™ process. Its aerosolised powder bulk density is preferably at least 10%, more preferably at least 20%, lower. It has been found that active substances according to the invention may, surprisingly, have both relatively low bulk powder densities yet also good powder flow properties in particular lower cohesiveness and adhesiveness and/or a lower tendency to accumulate static charge.

Specific surface area of particles may be determined by conventional surface area measuring techniques such as low temperature physical adsorption of nitrogen (eg, BET nitrogen adsorption using a Surface Area Analyser Coulter™ SA 3100 (Coulter Corp., Miami, USA)). Preferably the specific surface area of a particulate active substance according to the invention is at least 1.2 or 1.5 times, more preferably at least twice, still more preferably at least 3 times, most preferably at least 4 or 4.5 times, that of the same active substance produced by a non-SEDS™ process. Typically an active substance according to the invention might have a specific surface area of at least 10 $m^2/g$, preferably at least 15 or 20 or 25 $m^2/g$, and/or a surface-to-volume ratio of at least twice, preferably at least 2.5 times, that of spherical particles of the same volume diameter.

The shape factor f may suitably be calculated as f=Sv/Sv*, where Sv is the experimentally determined (eg, by BET nitrogen adsorption) specific surface area and Sv* the specific surface area calculated from particle size measurements (eg, those obtained by laser diffraction) assuming spherical particles. An active substance preferably has a shape factor f which is at least 20%, more preferably at least 30%, larger than that of the same active substance (suitably having the same or a comparable crystal shape and particle size) produced by a non-SEDS™ particle formation process. Thus, particles of an active substance according to the invention preferably have a higher available surface area than particles of the same active substance made by a non-SEDS™ process—where for instance the particles are in the form of platelets or needles, those of the present invention may thus be thinner than those produced by non-SEDS™ techniques.

A typical shape factor f for a particulate active substance according to the invention might for instance be 3 or greater, preferably 3.2 or greater, more preferably 3.5 or greater, most preferably 3.7 or greater.

A higher specific surface area and/or shape factor appears, in an active substance according to the invention, to accompany improved dissolution performance as compared to the same active substance produced by a non-SEDS™ particle formation process. In particular, a product according to the invention may dissolve more rapidly in any given solvent and with greater efficiency, for instance with at least 40% higher dissolution, more preferably at least 50% higher dissolution than the non-SEDS™ product after a period of 150 or even 300 minutes, ideally the SEDS™ product achieving complete dissolution after a period of 50 minutes or less. Such improved dissolution is particularly advantageous for poorly soluble (generally poorly aqueous soluble) materials.

Surface roughness may be assessed using AFM analysis; reduced roughness may be indicated for instance by a reduced RMS roughness. Particles of an active substance according to the invention preferably have a RMS roughness, measured using AFM, of 0.5 nm or less, preferably 0.3 or 0.2 nm or less. Their RMS roughness is preferably at least 70% lower, more preferably at least 80% or 90% lower, than that of the same active substance prepared by a non-SEDS™ particle formation process.

Deposition properties of an active substance, in particular fine particle fractions, may be measured using the cascade impactor technique, for instance using an Andersen™-type cascade impactor (Copley Scientific Ltd, Nottingham, UK). Such devices imitate particle deposition in the lungs from a dry powder inhaler. High fine particle fractions are preferred, with respect to delivery to stages 1 to 5 of the impactor. Thus, fine particle fractions are preferably measured as the mass of particles having an efficient cut-off diameter (ECD) of between 0.5 and 5 μm, for instance as described in the examples below. From the cascade impactor data, an apparent volume mean diameter may also be calculated as known in the art.

HPLC may be used for quantitative analysis of the active substance content in the material deposited at each stage of the impactor and if applicable in associated apparatus such as pre-separator, throat or mouthpiece.

For the purpose of assessing fine particle fraction, the active substance of the invention may be blended with a suitable excipient, preferably a pharmaceutically acceptable excipient suitable for delivery to the lung, a common example being lactose. Such a blend might typically contain from 1 to 10% w/w of the active substance, preferably from 2 to 5% w/w. Again because of the advantageous properties of the active substance of the invention, for instance its lower surface energy and adhesiveness, it tends to be better able to detach from the excipient, under these conditions, than the same active substance prepared by a non-SEDS™ process; in other words, it forms less strong aggregates with the excipient.

The active substance of the invention is preferably in the form of solid (eg, as opposed to hollow, porous or at least partially fluid-containing) particles. It is preferably in a crystalline or semi-crystalline (as opposed to amorphous) form, more preferably crystalline.

In particular it preferably has a crystalline form which is significantly longer in one dimension than in at least one other dimension (ie, it has a relatively high aspect ratio); this embraces for example needle-like crystals and also, potentially, wafer-, blade- or plate-like crystals (which are longer in two dimensions than in the third) and elongate prism-shaped crystals. These have been found to show better DPI performance than correspondingly sized particles of other shapes. Needle-like (acicular) or platelet-shaped crystals may be particularly preferred.

In the above discussion, "significantly" longer means at least 5%, preferably at least 10% or 20% or 30%, greater than the length of the lower of the two parameters being compared.

As discussed above, particles according to the invention if in the form of platelets or needles are typically thinner than those of the same active substance produced by a non-SEDS™ process (as reflected by for instance a difference in shape factors, shape coefficients and specific surface areas). When examined for example by SEM, the particles of the invention can often be seen to have less rounded edges and corners and/or to be less fragmented than those of the non-SEDS™ substance in particular a micronised substance—this may be reflected in a lower surface energy, lower particle adhesion and/or lower tendency for aggregation in the product of the invention.

In general, the behaviour of an active substance according to the present invention on aerosolisation, which in turn affects its suitability for respiratory drug delivery and in particular for DPI delivery, may be assessed and characterised using the techniques outlined in the examples below. These can involve assessing the size, surface characteristics, aerodynamic properties, deagglomeration behaviour and/or solid state properties of the active substance particles. Such techniques may be used for instance in the selection method of the second aspect of the invention.

By "active substance" is meant a substance capable of performing some useful function in an end product, whether pharmaceutical, pesticidal or whatever. The term is intended to embrace substances whose function may be as an excipient for another substance.

The active substance may be a single active substance or a mixture of two or more. It may be monomeric, oligomeric or polymeric, organic (including organometallic) or inorganic, hydrophilic or hydrophobic. It may be a small molecule, for instance a synthetic drug like paracetamol, or a macromolecule such as a protein or peptide (including enzymes, hormones, antibodies and antigens), nucleotide, nucleoside or nucleic acid. Other potential active substances include vitamins, amino acids, lipids including phospholipids and aminolipids, carbohydrates such as polysaccharides, cells and viruses.

The active substance preferably comprises (more preferably is) a pharmaceutically or nutriceutically active substance, or a pharmaceutically or nutriceutically acceptable excipient, or a mixture of two or more thereof. More preferably it is a pharmaceutically active substance or mixture thereof which is suitable for delivery by inhalation (which term includes nasal and/or oral inhalation), although in general it may be any active substance which is deliverable as a dry powder, ideally using a passive dry powder inhaler. Many other active substances, whatever their intended function (for instance, herbicides, pesticides, foodstuffs, imaging agents, dyes, perfumes, cosmetics and toiletries, detergents, coatings, products for use in the ceramics, photographic or explosives industries, etc.) are embraced by the present invention.

Of particular interest for delivery by inhalation are pharmaceutically active substances which need to be delivered systemically and require rapid onset of action. According to a preferred embodiment, formulations are provided which achieve a maximum concentration of a pharmaceutically active substance, $C_{max}$ within 1 hour of administration, preferably within 30 minutes, and most preferably within 15 minutes. This time to achieve maximum concentration of the active substance is referred to herein as $T_{max}$.

Examples of pharmaceutically active substances which may be delivered by inhalation include $\beta_2$-agonists, steroids such as glucocorticosteroids (preferably anti-inflammatories), anti-cholinergics, leukotriene antagonists, leukotriene synthesis inhibitors, pain relief drugs generally such as analgesics and anti-inflammatories (including both steroidal and non-steroidal anti-inflammatories), cardiovascular agents such as cardiac glycosides, respiratory drugs, anti-asthma agents, bronchodilators, anti-cancer agents, alkaloids (eg, ergot alkaloids) or triptans such as can be used in the treatment of migraine, drugs (for instance sulphonyl ureas) useful in the treatment of diabetes and related disorders, sleep inducing drugs including sedatives and hypnotics, psychic energizers, appetite suppressants, anti-arthritics, anti-malarials, anti-epileptics, anti-thrombotics, anti-hypertensives, anti-arrhythmics, anti-oxicants, anti-depressants, anti-psychotics, auxiolytics, anti-convulsants, anti-emetics, anti-infectives, anti-histamines, anti-fungal and anti-viral agents, drugs for the treatment of neurological disorders such as Parkinson's disease (dopamine antagonists), drugs for the treatment of alcoholism and other forms of addiction, drugs such as vasodilators for use in the treatment of erectile dysfunction, muscle relaxants, muscle contractants, opioids, stimulants, tranquilizers, antibiotics such as macrolides, am inoglycosides, fluoroquinolones and beta-lactams, vaccines, cytokines, growth factors, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents and mixtures of the above (for example the asthma combination treatment containing both steroid and β-agonist). More particularly, the active agent may fall into one of a number of structural classes, including but not limited to small molecules (preferably insoluble small molecules), peptides, polypeptides, proteins, polysaccharides, steroids, nucleotides, oligonucleotides, polynucleotides, fats, electrolytes, and the like.

Specific examples include the $\beta_2$-agonists salbutamol (eg, salbutamol sulphate) and salmeterol (eg, salmeterol xinafoate), the steroids budesonide and fluticasone (eg, fluticasone propionate), the cardiac glycoside digoxin, the alkaloid anti-migraine drug dihydroergotamine mesylate and other alkaloid ergotamines, the alkaloid bromocriptine used in the treatment of Parkinson's disease, sumatriptan, rizatriptan, naratriptan, frovatriptan, almotriptan, zolmatriptan, morphine and the morphine analogue fentanyl (eg, fentanyl citrate), glibenclamide (a sulphonyl urea), benzodiazepines such as vallium, triazolam, alprazolam, midazolam and clonazepam (typically used as hypnotics, for example to treat insomnia or panic attacks), the anti-psychotic agent risperidone, apomorphine for use in the treatment of erectile dysfunction, the anti-infective amphotericin B, the antibiotics tobramycin, ciprofloxacin and moxifloxacin, nicotine, testosterone, the anti-cholenergic bronchodilator ipratropium bromide, the bronchodilator formoterol, monoclonal antibodies and the proteins LHRH, insulin, human growth hormone, calcitonin, interferon (eg, β- or γ-interferon), EPO and Factor VIII, as well as in each case pharmaceutically acceptable salts, esters, analogues and derivatives (for instance prodrug forms) thereof.

Additional examples of active agents suitable for practice with the present invention include but are not limited to aspariginase, amdoxovir (RAPD), antide, becaplermin, calcitonins, cyanovirin, denileukin diftitox, erythropoietin (EPO), EPO agonists (e.g., peptides from about 10-40 amino acids in length and comprising a particular core sequence as described in WO 96/40749), domase alpha, erythropoiesis stimulating protein (NESP), coagulation factors such as Factor VIIa, Factor VIII, Factor IX, von Willebrand factor; ceredase, cerezyme, alpha-glucosidase, collagen, cyclosporin, alpha defensins, beta defensins, exedin-4, granulocyte colony stimulating factor (GCSE), thrombopoietin (TPO), alpha-1 proteinase inhibitor, elcatonin, granulocyte macrophage colony stimulating factor (GMCSF), fibrinogen, filgrastim, growth hormones, growth hormone releasing hormone (GHRH), GRO-beta, GRO-beta antibody, bone morphogenic proteins such as bone morphogenic protein-2, bone morphogenic protein-6, OP-1; acidic fibroblast growth factor, basic fibroblast growth factor, CD-40 ligand, heparin, human serum albumin, low molecular weight heparin (LMWH), interferons such as interferon alpha, interferon beta, interferon gamma, interferon omega, interferon tau; interleukins and interleukin receptors such as interleukin-1 receptor, interleukin-2, interluekin-2 fusion proteins, interleukin-1 receptor antagonist, interleukin-3, interleukin-4, interleukin-4 receptor, interleukin-6, interleukin-8, interleukin-12, interleukin-13 receptor, interleukin-17 receptor; lactoferrin and lactoferrin fragments, luteinizing hormone releasing hormone (LHRH), insulin, pro-insulin, insulin analogues (e.g., mono-acylated insulin as described in U.S. Pat. No. 5,922,675), amylin, C-peptide, somatostatin, somatostatin analogs including octreotide, vasopressin, follicle stimulating hormone (FSH), influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF), monocyte chemoattractant protein-1 endothelial growth factors, parathyroid hormone (PTH), glucagon-like peptide, somatotropin, thymosin alpha 1, thymosin alpha 1 IIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosphonates, respiratory syncytial virus antibody, cystic fibrosis transmembrane regulator (CFTR) gene, deoxyreibonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, afeliomomab, basiliximab, daclizumab, infliximab, ibritumomab tiuexetan, mitumomab, muromonab-CD3, iodine 131 tositumomab conjugate, olizumab, rituximab, and trastuzumab (herceptin), am ifostine, am iodarone, aminoglutethimide, amsacrine, anagrelide, anastrozole, asparaginase, anthracyclines, bexarotene, bicalutamide, bleomycin, buserelin, busulfan, cabergoline, capecitabine, carboplatin, carmustine, chlorambucin, cisplatin, cladribine, clodronate, cyclophosphamide, cyproterone, cytarabine, camptothecins, 13-cis retinoic acid, all trans retinoic acid; dacarbazine, dactinomycin, daunorubicin, dexamethasone, diclofenac, diethylstilbestrol, docetaxel, doxorubicin, epirubicin, estramustine, etoposide, exemestane, fexofenadine, fludarabine, fludrocortisone, fluorouracil, fluoxymesterone, flutamide, gemcitabine, epinephrine, L-Dopa, hydroxyurea, idarubicin, ifosfamide, imatinib, irinotecan, itraconazole, goserelin, letrozole, leucovorin, levamisole, lomustine, mechlorethamine, medroxyprogesterone, megestrol, melphalan, mercaptopurine, methotrexate, metoclopramide, mitomycin, mitotane, mitoxantrone, naloxone, nicotine, nilutamide, octreotide, oxaliplatin, pamidronate, pentostatin, pilcamycin, porfimer, prednisone, procarbazine, prochlorperazine, ondansetron, raltitrexed, sirolimus, streptozocin, tacrolimus, tamoxifen, temozolomide, teniposide, testosterone, tetrahydrocannabinol, thalidomide, thioguanine, thiotepa, topotecan, tretinoin, valrubicin, vinblastine; vincristine, vindesine, vinorelbine, dolasetron, granisetron; formoterol, fluticasone, leuprolide, midazolam, alprazolam, amphotericin B, podophylotoxins, nucleoside antivirals, aroyl hydrazones, sumatriptan; macrolides such as erythromycin, oleandomycin, troleandomycin, roxithromycin, clarithromycin, davercin, azithromycin, flurithromycin, dirithromycin, josamycin, spiramycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecia, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicllinase-sensitive agents like penicillin G, penicillin V; penicllinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, pentamidine isethiouate, albuterol sulfate; lidocaine, metaproterenol sulfate, beclomethasone diprepionate, triamcinolone acetamide, budesonide acetonide, fluticasone, ipratropium bromide, flunisolide, cromolyn sodium, and ergotamine tartrate; taxanes such as paclitaxel; SN-38, and tyrphostines.

The above exemplary biologically active agents are meant to encompass, where applicable, analogues, agonists, antagonists, inhibitors, isomers, and pharmaceutically acceptable salt forms thereof. In reference to peptides and proteins, the invention is intended to encompass synthetic, recombinant, native, glycosylated, non-glycosylated, and biologically active fragments and analogs thereof.

The active substance may comprise two or more active substances formulated together, such as one coated with another, or one dispersed within a matrix of another, or a physical mixture (blend) of two or more. Common examples of such formulations include two or more coformulated pharmaceutical actives, or pharmaceutically active substances coated with excipients, or physical mixtures of pharmaceutically active substances with excipients such as in particular lactose, or solid dispersions of pharmaceutically active substances with excipients, the excipient often being present to modify the release rate and/or to target delivery of the pharmaceutical. However, in general the active substances of the invention will exhibit improved dispersibility and DPI performance in the absence of excipients, ie, in the form of the active substance alone (for example in the form of a drug or drugs without excipients).

The improved dispersibility and DPI performance is preferably also exhibited in the absence of dispersion-enhancing or stabilising additives, such as surfactants or lubricants.

Preferably a particulate active substance according to the invention will exhibit improved dispersibility and DPI performance as compared to the same active substance, in particulate form, prepared by a non-SEDS™ particle formation process, in particular micronisation or granulation. By "micronisation" is meant a process involving mechanical means, for instance milling or grinding, to reduce particle size to the micrometer range. The non-SEDS™ substance may comprise particles having the same or a smaller size (for instance, 90% or less of the size of, or preferably 80% or 70% or 60% or less of the size) than those of the active substance of the invention.

In certain cases, an active substance according to the present invention may be a pharmaceutically active substance or a pharmaceutically acceptable excipient (preferably a substance suitable for and/or intended for delivery by inhalation) other than salmeterol xinafoate (alone or coformulated with hydroxypropyl cellulose); α-lactose monohydrate; R-TEM β-lactamase; maltose; trehalose; sucrose; budesonide; salbutamol sulphate; nicotinic acid; paracetamol (alone or coformulated with salmeterol xinafoate, L-poly(lactic acid), ethyl cellulose (EC), hydroxypropyl methyl cellulose (HPMC) or poly vinyl pyrrolidone (PVP)); ibuprofen; ketoprofen (alone or coformulated with EC, HPMC or PVP); salicylic acid; either indomethacin, carbamazepine, theophylline, ascorbic acid or a COX-2 selective inhibitor coformulated with EC, HPMC or PVP; quinine sulphate coformulated with EC; fluticasone propionate; omeprazole magnesium tetrahydrate; (S)-omeprazole magnesium trihydrate; formoterol fumarate dihydrate; felodipine; candesartan cilexetil; lysozyme; albumin; insulin; terbutaline sulphate; fenoterol hydrobromide; dihydroergotamine mesylate; and/or risperidone-(9-hydroxy)—palmitate.

It has been found that particulate active substances which exhibit the improved DPI performance and other advantageous properties described above can be produced using the so-called SEDS™ ("Solution Enhanced Dispersion by Supercritical fluid") process, which is a version of the GAS process referred to above.

SEDS™ is a process for forming particles of a "target" substance. It involves contacting a solution or suspension of the target substance in a fluid vehicle (the "target solution/suspension") with an excess of a compressed fluid (generally a supercritical or near-critical fluid) anti-solvent under conditions which allow the anti-solvent to extract the vehicle from the target solution/suspension and to cause particles of the target substance to precipitate from it. The conditions are such that the fluid mixture thus formed between the anti-solvent and the extracted vehicle is still in a compressed or supercritical or near-critical state. The anti-solvent fluid should be a nonsolvent for the target substance and be miscible with the fluid vehicle.

Carrying out a SEDS™ process specifically involves using the anti-solvent fluid simultaneously both to extract the vehicle from, and to disperse, the target solution/suspension. In other words, the fluids are contacted with one another in such a manner that the mechanical (kinetic) energy of the anti-solvent can act to disperse the target solution/suspension at the same time as it extracts the vehicle. "Disperse" in this context refers generally to the transfer of kinetic energy from one fluid to another, usually implying the formation of droplets, or of other analogous fluid elements, of the fluid to which the kinetic energy is transferred.

Suitable SEDS™ processes are described in WO-95/01221, WO-96/00610, WO-98/36825, WO-99/44733 and WO-99/59710, WO-01/03821 and WO-01/15664, in our co-pending PCT patent application no. PCT/GB PCT/GB01/04873 and in our co-pending UK patent application no. 0117696.5. Other suitable SEDS™ processes are described in WO-99/52507, WO-99/52550, WO-00/30612, WO-00/30613 and WO-00/67892, all of which are hereby incorporated in their entirety by reference.

In SEDS™, the target solution/suspension and the anti-solvent are preferably contacted with one another in the manner described in WO-95/01221 and/or WO-96/00610, being co-introduced into a particle formation vessel using a fluid inlet means which allows the mechanical energy (typically the shearing action) of the anti-solvent flow to facilitate intimate mixing and dispersion of the fluids at the point where they meet. The target solution/suspension and the anti-solvent preferably meet and enter the particle formation vessel at substantially the same point, for instance via separate passages of a multi-passage coaxial nozzle.

A particulate active substance according to the first aspect of the present invention is preferably prepared using a SEDS™ process, such as one or a combination of those described in the above documents, Preferred features of the process may be as described below in connection with the fourth aspect of the invention. The active substance may thus be insoluble or only sparingly soluble in water. It is preferably insoluble or only sparingly soluble in compressed (eg, supercritical or near-critical) carbon dioxide. Such materials lend themselves particularly well to SEDS™ processing and indeed are often difficult to process using other particle formation techniques such as spray drying or freeze drying.

Thus, a fourth aspect of the present invention provides the use of a SEDS™ process (as described above) to produce an active substance in particulate form, for the purpose of improving the dispersibility of the substance and/or its performance in a passive dry powder delivery device, and/or for the purpose of achieving one or more of the characteristics (a) to (q), optionally in combination with one or more of the other preferred properties, listed above in connection with the first aspect of the invention.

The process is preferably carried out using supercritical or near-critical, more preferably supercritical, $CO_2$ as the anti-solvent, The choice of operating conditions such as temperature, pressure and fluid flow rates, and the choice of solvent and of anti-solvent modifier if necessary, will depend on the nature of the active substance, for instance its solubility in the fluids present and, if it can exist in different polymorphic forms, which form is to be precipitated. Generally, the conditions should be chosen to minimise or reduce particle sizes and/or size distributions—this will generally mean selecting a higher anti-solvent flow rate (eg, a target solution/suspension: anti-solvent flow rate ratio (at or immediately prior to the two fluids coming into contact with one another) of 0.03 or less, preferably 0.02 or less or even 0.01 or less), and/or a higher operating temperature (eg, from 50 to 100° C., preferably from 70 to 90° C., especially for a $CO_2$ anti-solvent), and/or a higher operating pressure (eg, from 80 to 210 bar, preferably from 90 to 200 bar, again especially for a $CO_2$ anti-solvent).

The process conditions are also ideally chosen to maximise or enhance the purity (which may be the polymorphic or enantiomeric purity) of the product—this will involve the use of a vehicle, anti-solvent, temperature and pressure suitable to maximise or enhance selectivity of precipitation of the desired substance from those present in the target solution/suspension.

The operating conditions for the process (in particular the target solution/suspension concentration and the relative flow rates of the target solution/suspension and anti-solvent) are preferably selected, for any particular set of reagents (including the fluid vehicle and anti-solvent) and particle formation vessel and fluid inlet geometry, so as to maximise or enhance the degree of supersaturation in the target solution/suspension flow at its point of contact with the antisolvent. This may be effected for instance in the manner described in the examples below, using solubility measurements to determine the optimum operating conditions.

The product of the fourth aspect of the invention is preferably a particulate active substance according to the first aspect.

Improving the performance of a substance in a passive dry powder delivery device will typically mean increasing the fine particle fraction in the emitted dose when the active substance is delivered using a passive dry powder inhaler. The improvement may for instance be as compared to the performance of the substance prior to the SEDS™ processing, and/or of the same substance (preferably having the same particle size or a particle size no more than 10% or 20% or 30% or 40% different) when produced using another particle formation process such as micronising, granulation or conventional spray drying.

According to a fifth aspect of the present invention, there is provided an active substance for use in a method of surgery, therapy or diagnosis practised on a human or animal body, in which method the substance is delivered to a patient using a passive dry powder inhaler or analogous delivery device, wherein the substance has one or more of the properties described above in connection with the first to the fourth aspects of the invention.

A sixth aspect of the invention provides the use of an active substance in the manufacture of a medicament for use in a passive dry powder inhaler or analogous delivery device, wherein the substance has one or more of the properties described above in connection with the first to the fourth aspects of the invention.

For the fifth and sixth aspects of the invention, the active substance is preferably an active substance according to the first aspect, and is preferably prepared using the method of the fourth aspect and/or selected using the method of the second aspect. It is preferably a pharmaceutically or nutriceutically active substance. Other preferred features of the fifth and sixth aspects of the invention may be as described in connection with the first to the fourth aspects.

A seventh aspect of the present invention provides a dosage formulation or collection thereof, for use in a drug delivery device such as in particular a dry powder inhaler, the dosage formulation containing a particulate active substance according to the first aspect of the invention. Preferably the formulation consists essentially of the active substance, ie, it contains 95% w/w, preferably 98% w/w or 99% w/w, or more of the active substance. In particular, it may consist essentially of a pharmaceutically active substance in the absence of excipients and/or of dispersion enhancing or stabilising additives.

An eighth aspect of the invention provides an active substance (eg, drug) delivery device, preferably an inhaler, which contains one or more dosage formulations of an active substance according to the first aspect. The delivery device is preferably of the type designed to deliver a predetermined dose of an active substance in a dry (ie, without a fluid carrier) particulate form, for instance a dry powder inhaler and in particular a passive dry powder inhaler. It may contain one or more dosage formulations according to the seventh aspect of the invention.

According to a ninth aspect, the invention provides a method for delivering an active substance, the method involving charging a delivery device, in particular a device according to the eighth aspect of the invention, with an active substance and/or a formulation according to the invention and/or an active substance selected in accordance with the second aspect of the invention.

A tenth aspect provides a method of treatment of a human or animal patient, which method involves administering to the patient, preferably using the method of the ninth aspect of the invention, an active substance and/or a formulation according to the invention and/or an active substance selected in accordance with the second aspect of the invention.

Both of these methods preferably involve the use of a delivery device such as an inhaler, more preferably a delivery device according to the eighth aspect of the invention. The active substance preferably comprises a pharmaceutically active substance suitable for inhalation therapy.

The present invention will now be illustrated with reference to the following examples, which show how a SEDS™ process may be used to prepare particulate active substances with advantageous properties for use in passive dry powder inhalers.

EXAMPLES

The system used to carry out the SEDS™ particle formation processes was of the general type shown schematically in the figures of WO-95/01221.

Example 1

The SEDS™ method described in WO 95/01221 was employed to prepare powders of salmeterol xinafoate (SX, GlaxoSmithKline), terbutaline sulphate (TBS, AstraZeneca) and fenoterol hydrobromide (FHBr, Boehringer Ingelheim). The particle formation vessel of 0.5 L volume was used in all cases. Several solvents including methanol. Ethanol, acetone and tetrahydrofurane were tested, Typical flow rate of $CO_2$ was 5 kg/hour.

Analytical Methods PSD measurements were performed using firstly, AeroSizer time-of-flight instrument equipped with AeroDisperser™ (TSI Inc., Minneapolis, USA) and secondly, laser diffraction sensor Helos with dry-powder air-dispersion system Rodos (Sympatec GmbH. Germany). The volume mean particle diameter, VMD, was obtained for both instruments using software options. In the general case of non-spherical particles, these instruments cannot provide the exact value of VMD, however, the time-of-flight technique gives an aerodynamic-equivalent particle diameter, whereas the laser diffraction method provides the geometric projection-equivalent diameter. These diameters afford the complementary information on PSD and therefore can be used for comparative size analysis.

For SX powders, inverse gas chromatography (IGC) was performed using a Hewlett Packard Series 5890 Gas Chromatograph equipped with an integrator and flame ionization detector. For TBS and FHBr powders, IGC was done using a Hewlett Packard Series 6890 instrument which was specifically modified for IGC measurements by Surface Measurement Systems Ltd (Manchester, UK). The IGC method is described in detail by Tong et al. 2001. (Tong H. H. Y., B. Y. Shekunov, P. York, A. H. L. Chow, 2001. Pharm. Res. 18, 852.) Triplicate measurements in separate packed columns were made. Differences in surface energetics were reflected in the calculated dispersive component of the surface free energy, $\gamma_S^D$, specific component of surface free energies of adsorption. $\Delta G_A$; the acid-base parameters, $K_A$ and $K_O$ and the total (Hildebrand) solubility parameter, $\delta$, which reflects the adhesion work between particles. The $\gamma_S^D$ and $\Delta G_A$ values were obtained at 303K.

The deposition behaviour of micronised and supercritically-produced powders were evaluated using an Andersen-type cascade impactor (Copley Scientific Limited, Nottingham, UK). This device is designed to imitate particle deposition in the lungs; the control criterion is that the high fine particle fraction (FPF) of a respirable drug to be delivered to the defined stages (from 1 to 5) of the cascade impactor. The drugs were blended with inhalation grade, DMV Pharmatose® 325M α-lactose monohydrate, with 3.8% w/w of drug typical for such formulation. The airflow through the apparatus measured at the inlet to the throat, was adjusted to produce a pressure drop of 4 kPa over the inhaler under test (Clickhaler™) according to compendial guidelines, consistent with the flow rate 49 L/min.

Several batches of particulate material of respirable size with cumulative PSD for all batches $X_{99}$<10 μm were consistently prepared, with batch quantities between 1 and 10 g. VMD of powders obtained using different techniques are shown in Table 1.

TABLE 1

| Compound | VMD (μm) (Time of flight) | VMD (μm) (laser diffraction) | FPF (%) |
|---|---|---|---|
| SX Micronised | 1.2 | 1.69 | 25.1 |
| SX SEDS | 1.6 | 3.56 | 57.8 |
| TSB Micronised | 2.7 | 3.04 | 30.7 |
| TSB SEDS | 3.4 | 3.43 | 38.6 |
| FHBr Micronised | 1.7 | 2.34 | 17.4 |
| FHBr SEDS | 1.7 | 3.55 | 41.7 |

These data indicate that although both the aerodynamic (time of flight) and geometric (laser diffraction) diameters for the micronised panicles are smaller than the correspondent VMD for supercritically- produced materials, the FPF deposited in the cascade impactor is significantly larger for the supercritically-produced powders. Therefore the powder dispersion rather than the particle size distribution defines the deposition profile of the drug particles in this aerosol test. Dispersability of powders in the air flow is defined by the balance of forces generated by the aerodynamic stresses and the inter-particulate forces. The theoretical tensile strength of the particle aggregate, required to separate primary particles, is proportional to the work of particle adhesion (Kendell and Stainton, 2001) and can be associated with the specific surface energy defined by the IGC method. Table 2 represents the surface-energy related parameters which reflect the interaction of the non-polar $\gamma_S^D$ and polar $\Delta G_A$ nature.

TABLE 2

| Substance | $\gamma_S^D$ (mJ/m²) | $\Delta G_A$ (kJ/mol) | | | | | |
| | | Diethyl ether | Toluene | Acetone | Ethyl acetate | Chloroform | Dioxane |
|---|---|---|---|---|---|---|---|
| SX Micronised | 40.49 | 14.20 | | 15.24 | 17.46 | 14.78 | |
| SX SEDS | 34.55 | 12.65 | | (0.08) | (0.06) | (0.24) | |
| TSB Micronised | 58.61 | | 3.42 | 12.57 | 16.01 | 1.79 | 15.96 |
| TSB SEDS | 55.05 | | 2.85 | 10.42 | 13.76 | 1.21 | 14.20 |
| FHBr Micronised | 48.53 | | 4.77 | | | 0.69 | |
| FHBr SEDS | 49.87 | | 3.86 | 13.15 | 17.48 | 0.63 | 15.32 |

The reduced magnitude of $\gamma_S^D$ for the supercritically-produced powders implies that the surfaces of these particles are less energetic for non-polar, dispersive surface interactions than the micronised materials. The largest changes are however observed for the polar interactions $\Delta G_A$ which are significantly smaller, by a factor of 1.5 on average, for the supercritically-produced powders. In general, the enhanced powder dispersion always correlated well with the reduced surface energy of these materials.

Example 2

Salmeterol xinafoate (SX) (GlaxoWellcome, Ware UK) in the form of granulated material (G-SX) used for micronisation and micronised powder (M-SX). HPLC grade solvent was purchased from BDH Chemicals, Leicester, UK. All analytical grade liquid probes used in IGC studies were purchased from Labscan. Dublin, Ireland. Industrial grade (>99.95% pure) $CO_2$ was supplied by Air Products (Manchester, UK).

The SEDS™ method was employed to prepare powders of SX form I (S-SX). This technique is based on mixing between supercritical CO2 antisolvent and a drug solution using a twin-fluid nozzle as more fully described in WO 95/01221 cited above. Methanol, acetone and tetrahydrofurane were tested in this work. The particle formation vessel (500 ml volume) with the nozzle was placed in an air-heated oven. The temperature in the vessel was monitored by a thermocouple with accuracy ±0.1° C. and was kept constant at 40° C. Pressure in the vessel was controlled by an air-actuated back-pressure regulator (26-1761 with ER3000 electronic controller, Tescom. Elk River, Minn., USA) and kept constant at 250±1 bar. The difference in the inlet and outlet pressure was typically within 1% of its absolute value. The CO2 flow rate, supplied by a water-cooled diaphragm pump Milton Roy B (Dosapro Milton Roy, Pont-Saint-Pierre, France) was typically between 25 and 50 NL/min as monitored after expansion using a gas flow meter (SHO-Meter 1355, Brooks Instruments B. V., Veenendal, Holland) and also controlled before expansion using high-pressure liquid flow meter (DK34, Krohme Messtechnik GmbH, Duisburg, Germany). Solution concentration of SX varied between 1 and 10% w/v. Solution flow rate was provided by a metering pump PU-980 (Jasco Co, Tokyo, Japan) and varied from 0.5 to 10 ml/min.

Several batches were prepared with batch quantities between 1 and 10 g. The obtained cumulative PSD for all batches had $X_{90}\approx10$ μm and volume-moment mean particle diameter, $d_{4,3}\approx5$ μm, as determined using the laser diffraction (LD) method.

Inverse gas chromatography (IGC) was performed on a Hewlett Packard Series II 5890 Gas) Chromatograph (Hewlett Packard, Wilmington, Del., USA) equipped with an integrator and flame ionization detector. Injector and detector temperatures were maintained at 100 and 150° C. respectively. Glass columns (60 cm long and 3.5 mm i.d.) were deactivated with 5% solution of dimethyldichlorosilane in toluene before being packed with SX powder. The columns were plugged with silanised glass wool at both ends and maintained at 40° C. Data were obtained for a known weight and surface area of the sample using a nitrogen gas (purity>99.995%) flow at 20.0 ml/min. The column was weighed before and after the experiment to ensure no loss of materials during the run. Trace amount of vapour from non-polar and polar probes was injected. The retention times and volumes of the injected probes were measured at infinite dilution and thus were independent of the quantity of probes injected. The non-polar probes employed were pentane, hexane, heptane, octane and nonane: the polar probes were dichloromethane, chloroform, acetone, ethyl acetate, tetrahydrofuran and diethyl ether. Triplicate measurements in separate columns were made for G-SX. M-SX and S-SX powders. Differences in surface energetics were reflected in the calculated dispersive component of the surface free energy, $\gamma_S^D$; specific component of surface free energies of adsorption, $-\Delta G_A^{SP}$, and the acid-base parameters, $K_A$, and $K_D$.

Data on specific surface areas required for IGC studies were determined by BET nitrogen adsorption using a Surface Area Analyzer Coulter SA 3100 (Coulter Corp., Miami, Fla., USA). Samples were placed in glass sample holders and out-gassed with helium (purity>99.999%) at 40° C. for 16 hours before analysis. Nitrogen (purity>99.999%) was used as adsorbate and BET surface area was recorded as specific surface area of the samples. All measurements were performed in triplicate using the same batch of each material.

Electric Charge and Adhesion Measurements

Triboelectrification was undertaken against a stainless steel contact surface using either a turbula mixer or a cyclone separator. Triboelectrification in a turbula mixer (Glen Creston, UK) was carried out by agitating a powder sample for 5 minutes at 30 rpm in a 100 ml stainless steel vessel at ambient temperature and relative humidity. A sample was poured in a reproducible manner into a Faraday well connected to an electrometer (Keithley 610, Keithley Instruments, Reading, UK). Charge and mass of sample was then recorded to give specific charge before and after triboelectrification. % w/w adhesion to the inner surface of the mixing vessel was calculated from the original mass of sample and the mass of sample poured into the Faraday well. During triboelectrification in a cyclone separator, a powder was fed from a steel vibratory table into a venturi funnel. Compressed air (velocity 8 m/s. relative humidity below 10%, ambient temperature) was used to convey the powder from the venturi along a horizontal pipe into the cyclone separator. The Faraday well and force compensation load cell was fitted at the base of the cyclone and used to collect charged particles. Final specific charge was recorded for non-adhered powder residing in the Faraday well and, where possible, powder adhering to the cyclone wall was dislodged by a stream of air and its charge and mass recorded. In both cases, the results were obtained from triplicate measurements.

Particle Size Analysis

The instrument consisted of laser diffraction sensor HELLS and dry-powder air-dispersion system RODOS (Sympatec GmbH. Germany) with WINDOX OS computer interface. The dispersion process was controlled by means of adjusting pressure of the compressed air flow between 0.5 and 5 bar. The pressure of 2 bar was found to be sufficient to disperse most of the agglomerates avoiding, at the same time, attrition of the primary particles. All measurements were performed in triplicate. The particle shape factor, f, was calculated as f=Sv/Sv*, where Sv is the experimental specific surface area and Sv* is the specific surface area determined using the LD instrument assuming the particle sphericity.

Results and Discussion: Surface Free Energy and Specific Surface Area

The fundamental quantity of inverse gas chromatography is the net retention volume, $V_N$, determined from the retention time of a given solvent. Adsorption of the probe molecules on solid surfaces-can be considered in terms of both dispersive and specific components of surface free energy, corresponding to non-polar and polar properties of the surface. By virtue of their chemical nature, non-polar probes of the alkane series only have dispersive component of surface free energy, which can be determined from the slope of the plot based the following equation:

$$RTlnV_N = 2aN_A(\gamma_S^D)^{1/2}(\gamma_L^D)^{1/2} + \text{const}$$

where R is the gas constant. T is the column's absolute temperature, a is the probe's surface area. $N_A$ is the Avogadro's number, $\gamma_S^D$ is the dispersive component of surface free energy of a SX powder and $\gamma_L^D$ is the dispersive component of surface free energy of the solvent probes. Polar probes have both dispersive and specific components of surface free energy of adsorption. The specific component of surface free energy of adsorption ($\Delta G_A^{SP}$) can be estimated from the vertical distance between the alkane reference line and the polar probes of interest. This free energy term can be related to the donor number (DN) and acceptor number (AN*) of the polar solvent by the following equation:

$$\Delta G_A^{SP} = K_A DN + K_D AN^*$$

DN describes the basicity or electron donor ability of a probe whilst AN* defines the acidity or electron acceptor ability. Here, AN* denotes a correction for the contribution of the dispersive component and the entropy contribution into the surface energy is assumed negligible. Thus plotting—$\Delta G_A^{SP}/AN^*$ versus DN/AN* yields a straight line where $K_A$ and $K_D$ correspond to the slope and intercept respectively.

The IGC data for the various SX samples analysed by the above approach are summarized in Tables 3 and 4. Comparison between different materials shows that the magnitude of $\gamma_S^D$ is 15% smaller for S-SX compounds than for both M-SX and G-SX compounds. In addition, $\Delta G_A^{SP}$ for all polar probes used reduced by at least half for S-SX compound compared to the other two materials. Comparison between M-SX and G-SC materials indicates that, although the $\gamma_S^D$ are almost equal within the experimental error, $\Delta G_A^{SP}$ for all the polar probes is larger for the granulated material. The specific surface area, a, is twice as small for the S-SX compound compared with both M-SX and G-SX materials indicating that the mean surface-equivalent particle diameter for these compounds is smaller than for S-SX compound.

The reduced magnitude of $\gamma_S^D$ for S-SX compound implies that the surfaces of these panicles are less energetic for non-polar, dispersive surface interactions than the other two compounds. The overall strength of the polar interactions $\Delta G_A^{SP}$ is also the smallest for S-SX compound. Comparison between the $K_A$ and $K_D$ values of the three samples indicate that the acidity constant has the following trend: $K_A$(S-SX)<$K_A$(M-SX)<$K_A$(G-SX). The basicity constants follows the reverse order with $K_D$(S-SX) being the largest. Thus S-SX sample which has the weakest acidic property exhibits the strongest basic interactions with respect to its exposed polar groups at the interface. This suggests that S-SX crystal surfaces have, in relative terms, more exposed basic groups but fewer exposed acidic groups than both G-SX and M-SX compounds. Particles of all three compounds have a similar platelet shape with the dominant {101} crystal faces. However, S-SX particles have the largest shape factor, f (see Table 3), which means that platelets of G-SX and M-SX are thicker. The other materials have more energetic lateral crystal surfaces as a result of the solution crystallisation procedure (G-SX) and particle breakage on micronisation (M-SX). Therefore the observed differences in $K_A$ and $K_D$, combined with the smallest magnitude of $\Delta G_A^{SP}$ and $\gamma_S^D$ for S-SX compound, suggests a combination of three different factors affecting the specific surface energy: (a) difference in the crystal habit. i.e. the {001} crystal faces have stronger basic and weaker acidic interactions than the lateral crystal faces, (b) smaller overall specific surface energy of the {001} crystal planes as compared to any other crystallographic planes and (c) disturbances of the crystal structure which also contribute to the higher surface energy of G-SX and M-SX compounds.

It is clear that solvent adsorption- progress more rapidly with the M-SX and G-SX samples than with S-SX material. This fact indicates that supercritical fluid process of the invention produces particles with lower surface activity (and greater surface stability) than powders produced by solution crystallisation and micronisation.

TABLE 3

| Compound | $\gamma_S^D$ (mJ/m²) | $K_A$ | $K_D$ | $S_V$ | f |
|---|---|---|---|---|---|
| S-SX | 32.476 | 0.110 | 0.356 | 7.040 | 3.78 |
| M-SX | 38.285 | 0.172 | 0.298 | 9.243 | 2.80 |
| G-SX | 36.972 | 0.233 | 0.157 | 10.699 | — |

TABLE 4

| | $-\Delta G_A^{SP}$ (kJ/mol) | | | | | |
|---|---|---|---|---|---|---|
| | Dichloro-methane | Chloro-form | Acetone | Ethyl acetate | Diethyl ether | Tetrahydrofuran |
| S-SX | 2.808 | 0.153 | 3.797 | 2.705 | 1.488 | 2.446 |
| M-SX | — | 0.810 | 4.560 | 3.995 | 2.774 | 3.609 |
| G-SX | — | 1.885 | 5.454 | 4.739 | 2.958 | 4.854 |

Table 5 presents results on the charge, Q, and fraction of adhered material, AD. S-SX particles exhibited significantly less (between one and two orders of magnitude) accumulated charge than the micronised powder before and after turbula mixing and also for the non-adhered drug in cyclone separator. Correspondingly, the fraction of adhered material is several times smaller for S-SX powder than for M-SX powder in both the turbula mixing and cyclone separator tests.

These results are consistent with the superior powder flow properties of S-SX material. Although the bulk powder density of S-SX material is very low (about 0.1 g/cm³ vs. 0.5 g/cm³ for M-SX) it flows well and does not adhere to the container walls.

TABLE 5

| | Turbula Mixer | | | Cyclone Separator | | |
|---|---|---|---|---|---|---|
| | Q (nCg⁻¹) Before mixing | Q (nCg⁻¹) After mixing | AD (% w/w) | Q (nCg⁻¹) Before mixing | Q (nCg⁻¹) After mixing | AD (% w/w) |
| S-SX | −0.52 | −0.17 | 1.5 | 4.9 | −34.6 | 5.5 |
| M-SX | −12.1 | −42.6 | 27 | −48.4 | −49.7 | 16.7 |

Particle Size and Powder Dispersability

The difference in PSD of S-SX and M-SX powders is reflected in the magnitude of the mean particle sizes $d_{4,3}$=3.5 μm (S-SX) and 1.8 μm (M-SX) and as measured using the LD technique. For both materials the cumulative PSD>98% within respirable particle size range 0.5<x<10 μm. However, a significant difference was observed between the dispersion behavior of micronised and supercritically-process- ed powders. At high dispersing pressures above ≈2 bar, $d_{4,3}$ is smaller for M-SX powder, as indicated by the primary PSD for this compound. This situation changes dramatically at dispersing pressures below 2 bar. At low pressures, S-SX powders consistently produce a large fraction of primary particles in the respiratory size range, whereas M-SX powders form stable agglomerates outside the 5 μm range which cannot be dispersed at such pressures.

The enhanced dispersability of S-SX powders-means a decrease of the inter-particulate contact area and/or reduction of the cohesive forces leading to better performance of S-SX compound in the inhalation devices. Despite a larger geometric (and volume) diameter for S-SX particles, the Andersen cascade impactor measurements indicated a greater than two-fold increase (from 25.15 to 57.80%) of FPF for S-SX powder compared with FPF of M-SX powder.

Example 3

This example measured the surface charge and adhesiveness of particles of the drug salbutamol sulphate produced using a SEDS™ process as compared to that of both the unprocessed starting material and a micronised sample of the drug.

Surface charge was examined by placing weighed portions of the samples in a Faraday well to measure their electrostatic charge.

A simple adhesion test was devised to examine the observation that the ultra-fine powders prepared by the SEDS™ process exhibited low adhesion to containers and vessel walls, and low adhesive interaction with surfaces in general. In this test, a small quantity of powder was weighed into a screw topped glass jar and the jar rotated for 5 minutes. The non-adhering powder was then tipped from the jar and weighed and the percentage powder adhering to the walls of the jar calculated.

The results of both the charge and the adhesion tests are shown in Table 6 below. It can be seen that both the unprocessed and the micronised materials exhibited relatively high surface charge, whilst the figure for the SEDS™ sample was dramatically reduced. Further, in the adhesion tests, there was minimal adhesion of the SEDS™-processed material, whilst significant amounts of the micronised form of the same material adhered to the surfaces of the jar.

These findings are consistent with the surprisingly observed easy flowing nature of SEDS™ products, being different from the generally observed highly charged, cohesive and non-free flowing nature of micronised materials of a similar particle size.

TABLE 6

| Sample | Electrostatic Charge (nC/g) | Relative Powder Adhesion (to container walls) |
|---|---|---|
| Unprocessed | −23.1 | 8.6 |
| Micronised | −42.6 | 18.6 |
| SEDS | −0.2 | 1.0 |

Example 4

This example measured the specific surface area (by low temperature physical adsorption of nitrogen) of a poorly aqueous soluble drug produced using a SEDS™ process, as compared to a micronised sample of the same drug.

The specific surface area of the micronised sample was 5.6 m$^2$/g, whereas that of the SEDS™ sample was 27.8 m$^2$/g.

Example 5

These examples assessed the dissolution performance of an aqueous soluble compound produced using a SEDS™ process and also in a micronised form. A conventional test method was used, as described in the current pharmacopoeia and compendia (eg, BP and USP). Three SEDS™-produced samples were tested.

The results are shown in FIG. 1, which plots the percentage dissolution against time. The ultra-fine particulate products of the invention clearly dissolves much more rapidly and efficiently than the micronised version of the same substance, exhibiting much faster dissolution profiles to complete dissolution. A further advantage of the SEDS™ products is the consistency of their dissolution profiles between repeat batches.

Example 6

These examples assessed the surface roughness of a SEDS™-produced material as compared to that of (a) the crystallised starting material and (b) the same compound in a micronised form. Conventional AFM analysis was used for the assessments.

Figure 2:
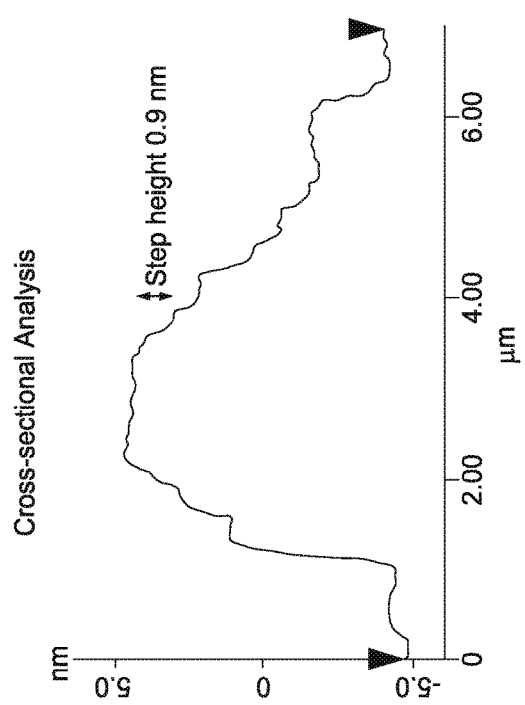
FIG. 2 depicts an AFM analysis of material process according to this invention.
Figure 3:
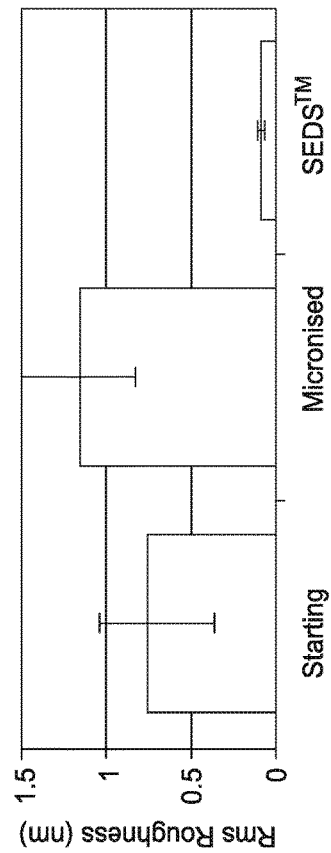
FIG. 3 is a graph showing RMS surface roughness data for materials processed according to the invention.

The results are shown in FIGS. 2 (AFM analysis of the SEDS™-processed material) and 3 (graph showing RMS surface roughness data for the three samples) below. The SEDS™ sample clearly had a smoother topographical character.

Example 7

The properties of a micronised sample of salbutamol sulphate were compared with those of a SEDS™-processed sample of the same drug. The SEDS™ sample was prepared from a 10% w!v solution of salbutamol sulphate in acetone, using a 568 ml particle formation vessel, a two-passage concentric nozzle with a 0.1 mm internal diameter orifice, a processing temperature of 50° C. and pressure of 150 bar, a drug solution flow rate of 0.04 ml/min and a supercritical carbon dioxide anti-solvent flowing at 18 ml/min.

The mean amorphous content of the micronised sample, determined by the dynamic moisture sorption method, was 6.92%, w/w (standard deviation 1.10). That of the SEDS™ sample in contrast was only 0.13% w/w (SD 0.05).

The mean value for $\gamma_s^D$ (the dispersive component of surface free energy, determined by IGC) was 58.57 mJm$^{-2}$ (SD 2.19) for the micronised sample but only 38.45 mJm$^{-2}$ (SD 1.50) for the SEDS™ sample.

The mean specific charge of both samples was +4.00 nCg$^{-1}$ before mixing. After triboelectrification by Turbula™ mixing this value had increased to +25.9 nCg$^{-1}$ for the micronised sample but only +16.4 nCg$^{-1}$ for the SEDS™-produced sample.

Further, blends of salbutamol sulphate with lactose (both a micronised and a SEDS™-produced sample) were tested in an Andersen-type cascade impactor with a Clickhaler™ DPI device. The fine particle fraction of the emitted dose was measured as 11.86% for the micronised sample and 33.57% for the SEDS™ one.

Example 8

The respiratory drug terbutaline suplphate (TBS) was prepared by SEDS™ process and its properties and DPI performance compared to those of a micronised sample of the same drug. The DPI performance of blends of TBS with the carrier alpha-lactose monohydrate was also investigated, since the drug-carrier adhesion and hence the particulate (especially surface) properties of the drug and carrier; can significantly influence their dispersibilty in DPI systems.

Production of Powers
Materials

The material studied was supplied as solution (2% w/v) was delivered by a separate reciprocating HPLC pump (Janco PU-980, Japan) and varied between 0.1 and 4.8 ml/min. Liquid $CO_2$ (−10° C.) was pumped by a water-cooled Dosapro Milton Roy pump (Type: MB 112S (L) 10 M 480/J VV2, Pont-Saint-Pierre, France) and flow was varied between 4.5 and 80 ml/min. The $CO_2$ passed through a heat exchanger to ensure that it was supercritical before entering the nozzle, which consisted of two concentric tubes and a small premixing chamber. Two nozzle diameters, 0.1 and 0.2 mm were used in the study. The powder (typically about 200 mg a batch) was collected from the vessel and analysed. A range of operating temperatures (35-80° C.) and pressures (80-250 bar) were applied to produce drug powder using the SEDS™ process.

Physical Characterisation of Powders
Particle Size Analysis
Laser Diffraction

A small amount of TBS powder was analysed using a laser diffraction RODOS/VIBRI dispersing system (HELOS/RODOS, Sympatec GmbH, Clausthal-Zellerfeld, Germany). The instrument consisted of a laser sensor HELOS and a RODOS dry-powder air-dispersion system (Sympatec GmbH, Clausthal-Zellerfeld, Germany). Different measurement ranges of the laser sensor were provided by interchangeable objectives R1 (0.1-35 µm) and R2 (0.25-87.5 µm). The rate of powder dispersion was controlled by adjusting the pressure of the compressed air flow. A pressure of 2 bar was sufficient to achieve deagglomeration of primary particles without attrition.

Time-of-Flight Measurements

The TBS samples were also analysed using an AeroSizer™ (Amherst Process Instruments, Amherst, Mass., USA), provided with pulse jet disperser, the AeroDisperser™, to introduce the powders to the instrument. The were analysed for 300 seconds in triplicate using normal deagglomeration conditions, feed rate (5000 particles per second) and medium shear force (0.5 psi).

micronised powder of terbutaline sulphate (AstraZeneca R & D, Lund, Sweden), α-lactose monohydrate (Pharmatose 325 M inhalation grade DMV International, Veghel, The Netherlands) was used as a carrier for the cascade impaction studies. Carbon dioxide (BOC Ltd, UK) was 99.9% pure and methanol, ethanol and water were of HPLC grade (Fischer Scientific Limited, Loughborough, UK). Chloroform, toluene, ethyl acetate, acetone and 1,4-dioxane, of HPLC grade (99+% purity) were used as polar probes whereas a series of n-alkanes from hexane (n=6) to decane (n=10) of HPLC grade (99+% purity) were used as non-polar probes for IGC analysis.

Solution Enhanced Dispersion by Supercritical Fluids (SEDS™) Process

Figure 4:
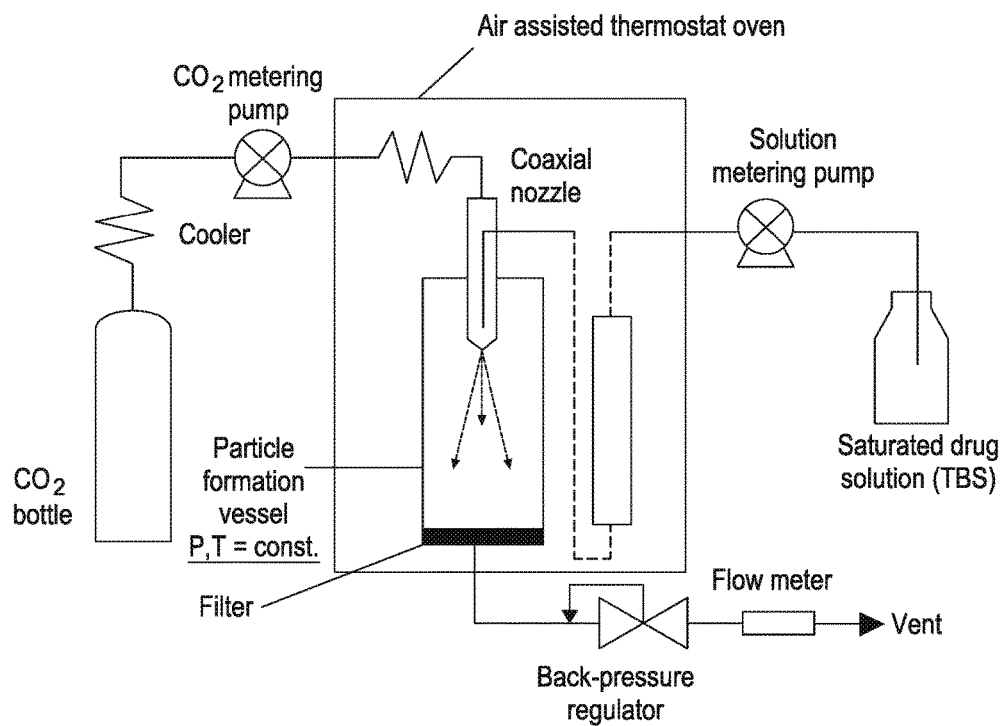
FIG. 4 is a schematic of the SEDS process.

For experiments that used ethanol as a solvent, the SEDS™ process was modified in such a way that an additional extraction vessel packed with TBS powder was placed in an oven and pure ethanol was pumped through the vessel. This enhanced extraction of TBS and resulted in product yield >85% w/w (see FIG. 4, vessel position indicated by dotted lines). All other experiments were conducted in a SEDS™ apparatus as disclosed in WO 95/01221 consisting of a stainless steel particle formation vessel (50 ml) positioned in an air assisted heated oven with a specially designed two flow coaxial nozzle capable of withstanding a pressure of 500 bar. Pressure in the system was maintained within ±1 bar by an automated back-pressure regulator (Tescom, Japan). Drug Scanning Electron Microscopy (SEM)

A small amount of powder was manually dispersed onto a carbon tab adhered to an aluminium stub, (Agar Scientific, UK). The sample stubs were coated with a thin layer (200 Å) of gold by employing an Emitech K550 sputter coater (Texas, USA). The samples were examined by SEM (Hitachi S-520, Tokyo, Japan) and photographed under various magnifications with direct data capture of the images onto a personal computer.

Solid State Analysis

X-Ray Powder Diffraction (XRPD)

Structural analysis of the samples was performed using an X-ray powder diffractometer (Siemens, D5000, Karlsruhe, Germany), fitted with a rotating sample holder, a scintillation counter detector and a divergent beam utilising a CuKα source of X-rays (λ=1.5418 Å). Each sample was placed in the cavity of an aluminium sample holder flattened with a glass slide to present a good surface texture and inserted into the sample holder. In order to measure the powder pattern, the sample holder and detector were moved in a circular path to determine the angles of scattered radiation and to reduce preferred sample orientation. All samples were measured in the 2θ angle range between 1.5° and 45° with a scan rate of 3 seconds/step and a step size of 0.05°. Samples were analysed in duplicate.

Differential Scanning calorimetry (DSC)

Prior to sample analysis, a baseline was obtained which was used as a background. DSC analyses of terbutaline sulphate samples were carried out on a Perkin Elmer 7 Series differential scanning calorimeter thermal analysis system (Perkin Elmer Ltd., Beaconsfield, UK). Temperature and enthalpy were calibrated with the standard materials indium (melting point=156.6° C.) and zinc (melting point=419.5° C.). Samples (1-10 measurement range of the AeroSizer™ is nominally from 0.2 to 200 μm of aerodynamic diameter with the standard 750 μm diameter tapered nozzle. The micronised and SEDS™ TBS samples mg) were accurately weighed into pierced, crimped aluminium pans and heated at 10° C. min$^{-1}$ over a heating range of 25-290° C. under a nitrogen purge. A chiller unit was used in conjunction with the calorimeter to attain the lower temperatures.

Dynamic Vapour Sorption (DVS)

The moisture sorption isotherm of each powder at 25° C. was measured using a dynamic vapour sorption (DVS) instrument made by Surface Measurement Systems, UK. This instrument gravimetrically measures uptake and loss of water vapour on a substrate by means of a recording microbalance with a resolution of ±0.1 μg. In the first step of the experimental run, the sample was dried at 25° C. and 0% relative humidity (RH) for at least 600 minutes to bring the sample to near zero wt % $H_2O$. Then, the instrument was programmed to increase the RH in steps of 5% RH from 0% to 90% RH and decrease the RH in steps of 10% RH from 90% to 0% RH. A criterion of dm/dt=0.005%/min was chosen for the system to hold at each RH step before proceeding to the next RH step. Sample masses between 30 and 100 mg were used in this study. The change in mass (%) is expressed in terms of g $H_2O$ per 100 g of dry substance.

Isothermal Microcalorinietry

A Thermal Activity Monitor (TAM, model 2277; Thermometric A B, Jrflla, Sweden) was used to measure the calorimetric heat flow (μW) vs. % RH profile of each sample. A RH-perfusion cell (Model 2255-120) accessory for the TAM was used to control RH within the sample vessel. The carrier gas, dry $N_2$, was flowed at a constant rate (1.48 cm$^3$/min). All experiments were performed at 25° C. About 100 to 105 mg accurately weighed of each powder were placed in a stainless steel ampoule, attached to the RH perfusion cell, and then dried under 0% RH until a stable heat flow signal was reached (e.g., a signal within the range of −1 to +1 μW). The RH was then increased in a linear ramp from 0 to 90% over the following 30 hours (i.e., 3% RH/hr). The heat flow arising from interactions of water vapour with the solid sample was measured as a function of time. Since RH changed with time in a linear fashion, the heat flow was also known as a function of RH.

The TAM measures the total heat flow in power, P, produced from either a physical or chemical reaction. In this study the calorimetric power is proportional to the rate of moisture sorption or desorption, crystallization, and/or other processes. Exothermic events are measured as a deflection in the positive y-axis direction. Although crystallization is an exothermic process, it can be observed as a net endothermic process. During crystallization, there is an exotherm due to crystallization and a simultaneous endotherm due to desorption of previously sorbed moisture. The TAM profile gives the resultant of these processes. Hence, for crystallization, the TAM profile can be an exothermic peak only, an endothermic peak only or a sequential combination of both exothermic and endothermic peaks.

Inverse Gas Chromatography (IGC)

An empty GC column was uniformly packed with the powder of interest (TBS). Pre-silanised commercially available straight glass columns of 30 cm length with a 3 mm internal diameter were used in this investigation. The silanation procedure was necessary to minimize active sites on the inner glass surfaces, which strongly interact with polar probes. Each column was packed at the detector end with a small amount of silanised glass wool, was clipped to a stand and powder was added through a glass funnel with the aid of a mechanical column packer (tapping) to improve powder flow and remove any air gaps. Once the column had been filled, the injector end of the column was also packed with silanised glass wool and attached to a separate, purpose built column oven that controls the sample (column) temperature between room temperature and 90° C. A. Hewlett Packard 6890 Series Gas Chromatograph (GC) (Hewlett Packard, Penna, USA) oven equipped with an autosampler was used to control the solvent temperature. The 6890 GC data acquisition system was used to record data from a thermal conductivity detector (TCD) and flame ionisation detector (FID) with the instrument modified for IGC by Surface Measurement Systems (SMS), Manchester, UK. The combination of detectors allowed sensitive analysis of both organic vapour elution and water (although RH was not raised above 0% for these experiments).

The whole system was fully automated by control software (SMS iGC Controller v1.3) and the data analysed using SMS iGC Analysis macros. Prior to analysis, each column was equilibrated at 30° C. and 0% relative humidity (RH) for 5 hours by passing dry helium gas through the column. Helium gas was also used as the carrier gas. Hydrogen and compressed air flow rates were set at 40 and 450 ml min$^{-1}$ respectively for the FID. The chromatograph injection port was maintained at 80° C., TCD detector at 150° C. and the FID detector at 150° C. Column temperature was set at 30° C. throughout analysis. Data were obtained by flowing helium gas at 10 ml min through the sinalised glass column packed with a known weight of powdered material and injecting small amounts (concentration P/Po=0.05) of a range of probe vapours with different polarities. The retention times of the probes were measured using SMS iGC Controller v1.3 software, at infinite dilution or near zero surface coverage (equivalent to $10^{-4}$-$10^{-7}$ µl of liquid) where retention is independent of the quantity of probe injected. For each sample, two columns were prepared and analysed by employing a method based on standard settings, which allows the precise control and measurement of experimental variables. This is essential in producing meaningful results. The data were used to calculate the dispersive and non-dispersive forces acting at TBS particle surfaces using the method developed by Schultz and co-workers (J. Schultz, L. Lavielle and C. Martin. The role of the interface in carbon fibre-epoxy composites, J. Adhesion, 23, 45-60 (1987)).

Powder Analysis

Aeroflow Method

An Aeroflow™ powder avalanching apparatus (Amherst Process Instruments, API, Amherst, USA) was employed to analyse the dynamic avalanching behaviour of micronised and SC processed TBS samples. The Aeroflow apparatus consists of a transparent rotating drum with a port at the front. A white light source is positioned in front of the drum and a masked array of photocells is behind the drum. To measure avalanching, 50 ml of the drug powder was added to the drum, which is about 15% of its total volume to ensure good powder mixing during the operation. As the drum rotates, the powder bed is carried upwards until an unstable state is reached and an avalanche occurs.

The time between successive avalanches was recorded by the projection of the light beam through the drum onto the photocell array. The photocells generated a voltage dependent on the amount of light falling on the cells and the area of unmasked photocells shielded from the light source by the powder. The voltage output (transmitted light intensity) was recorded by a computer, which translates the output as powder movement using a technique disclosed in B. H. Kaye. Characterising the flowability of a powder using the concepts of fractal geometry and chaos theory, Part. Part. Charact. 14: 53-66 (1997). Each TBS sample was tested in duplicate and mean avalanche time and irregularity (scatter) of avalanches were recorded.

Powder Dispersion by Cascade Impaction

An Andersen Cascade Impactor (1 ACFM Eight Stage Non Viable Andersen Cascade Impactor, Copley Ltd, Nottingham, UK) was used to determine the dispersability and fine particle fraction (FPF) of each powder/carrier blend and pure drug alone through a dry powder inhaler device (Clickhaler®, Innovata Biomed, St, Albans, UK). To prevent particles from bouncing off the plates and becoming re-entrained in the air stream prior to each analysis, the eight metal plates of the impactor were coated with a thin layer of silicone spray and left to dry for 30 minutes. A pre-separator was attached to the top of the impactor to prevent large particles or aggregates from reaching the stages. The air flow through the apparatus, measured at the inlet to the throat, was adjusted to generate a pressure drop of 4 kPa over the inhaler under test and a duration consistent with the flow of 4 liters min$^{-1}$ according to compendial guidelines (Pharm Forum, 22: 3049-3095 (1996). These conditions are consistent with a flow rate of 49 1 min$^{-1}$ and 4.9 s duration. A blend containing 3.8% w/w of compound, hand-filled into the reservoir of a Clickhaler® device, which is capable of delivering 200 µg of drug per actuation, was used. Ten doses were discharged into the apparatus and each determination was carried out at least twice. After each determination, the powder on each impaction stage was collected by rinsing with mobile phase and the resulting solutions were analysed by HPLC. The amount of drug deposited in the throat piece and the pre-separator was also determined.

The Andersen cascade impactor is traditionally calibrated at 28.3 1 min$^{-1}$ but may be operated at higher flow rates, which are thought to more closely approximate a patient's capabilities (F. Podczeck. Optimisation of the operation conditions of an Andersen-Cascade impactor and the relationship to centrifugal adhesion measurements to aid the development of dry powder inhalations, Int. J. Pharm., 149: 51-61 (1997)). Using a variation of the Stokes' equation, effective cut-off diameters (ECDs) at the higher flow rate can be calculated from the equation given below (M. M. Van Oort, B. Downey, and W. Roberts. Verification of operating the Andersen Cascade Impactor at different flow rates, Pharm. Forum, 22: 2211-2215 (1996).

$$ECD_{F2}=ECD_{28.3}(28.3/F2)^{1/2}$$

where $ECD_{F2}$ is the ECD at the alternative flow rate, $ECD_{28.3}$ is the manufacturer's flow rate (28.3 1 min$^{-1}$) and F2 is the alternative flow rate in 1 min$^{-1}$. The alternative flow rate used in this study was 49.1 min$^{-1}$. Particles collected on the filter were smaller than 0.32 µm. The percentage of the total dose collected on the stages 1 through 5 represented particles with the aerodynamic diameters less than 4.36 µm, and was considered as the fine particle fraction (FPF).

Results and Discussion

Powder Preparation and Optimisation

TBS was produced using the SEDS™ process. Different solvents such as pure methanol, methanol/water, pure water and pure ethanol were used to dissolve drug material between 1-10% w/w in concentration. To optimise the particle properties (crystallinity, shape, size, size distribution) a number of parameters such as concentration of the drug, drug solution flow rate, $CO_2$ flow rate, temperature and pressure of the system were manipulated. A wide range of SEDS™ products such as a hydrated crystal, amorphous material, and two previously reported polymorphs A and B were produced using different solvents and experimental conditions. For example, the clear difference in morphology and crystallinity (determined by XRPD which was based on diffraction peaks area and DSC by measuring change in enthalpy of fusion) of TBS1 (127.12 J/g) and TBS2 (88.68 J/g) may be attributed primarily to the different residence time for particle formation and mixing in vessels which is defined as $\tau=V/f$, where V is the volume of the vessel and f is the volumetric flow rates of ethanol and $CO_2$ at given temperature and pressure respectively. Particles in the smaller 50 ml vessel were exposed to partially mixed ethanol-rich phase which exist in the core of high velocity jet (B. Y. Shekunov, J. Baldyga, and P. York. Particle formation by mixing with supercritical antisolvent at high Reynolds numbers, Chem. Eng. Sci., 56: 2421-2433 (2001)), whereas the particles in the large 500 ml vessel were accumulated in well mixed $CO_2$-rich phase.

SEM photomicrographs of a typical micronised and SCF processed batches of TBS were obtained. The use of different solvents such as pure methanol and methanol/water resulted in needle-like as well as-spherical amorphous particles respectively. Particles obtained using pure methanol, pure ethanol and pure water have revealed well-defined crystal edges compared to micronised particles.

Particle Size

The average particle size by volume determined by laser diffraction for a typical batch of TBS1 and TBS2 was between 3.2 and 3.4 μm with 90% less than 7 μm in comparison to 3.0 μm microparticles of micronised terbutaline sulphate with 90% less than 5 μm. This method showed good reproducibility and therefore, was used for the quality control assessment.

The samples were also analysed with the AeroSize™. Micronised, TBS1 and TBS2 samples have similar aerodynamic diameters to those obtained by the Sympatec™ laser diffraction instrument. However, TBS3, TBS4 and TBSS showed larger mean diameters by AeroSizer™ in comparison to laser diffraction analysis. These results are depicted in Table 7 below. The AeroSizer™ gives an aerodynamic equivalent diameter, which is smaller than geometric volume diameter for non-spherical primary particles. Therefore, the results here likely indicate insufficient dispersion by AeroDisperser™ of the agglomerated particles of both batches TBS4 and TBSS. In addition, the sampling procedures in the AeroSizer™ nozzle may produce discrepancies in time-of-flight measurements at large particle number densities, which is the case of small amorphous particles in TBS4. Therefore, the reproducibility of results for this technique was lower than for the laser diffraction method.

TABLE 7

| Sample | Sympatec $D_{4,3}$ (μm) | Aerosizer $D_{4,3}$ (μm) |
| --- | --- | --- |
| Micronised | 3.04 | 2.69 |
| TBS 1 | 3.22 | 3.31 |
| TBS 2 | 3.43 | 3.44 |
| TBS 3 | 1.99 | 6.69 |
| TBS 4 | 4.75 | 15.53 |
| TBS 5 | 4.84 | 11.44 |

X-Ray Diffraction and DSC Profiles

Figure 5A:
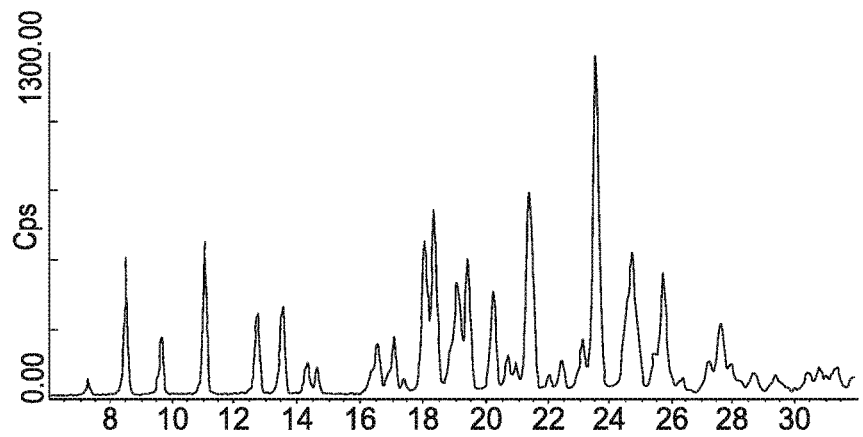
FIGS. 5A-5C depict X-ray powder patterns illustrating the crystallinity of micronised and samples produced according to the invention.
Figure 5B:
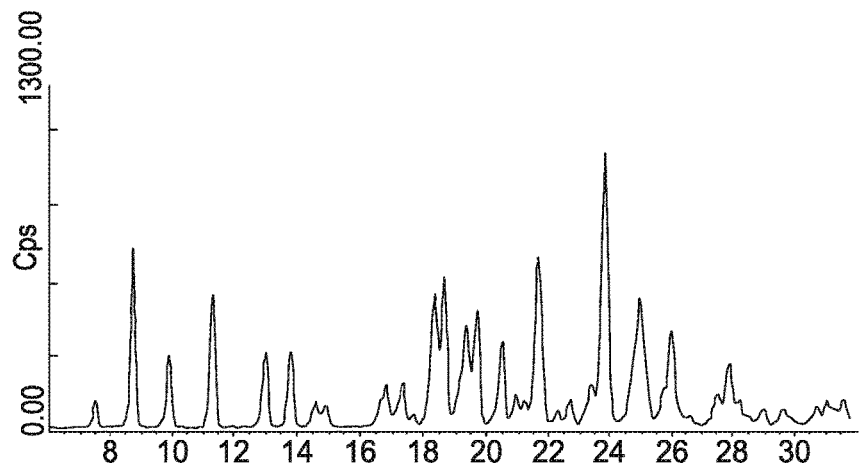
Figure 5C:
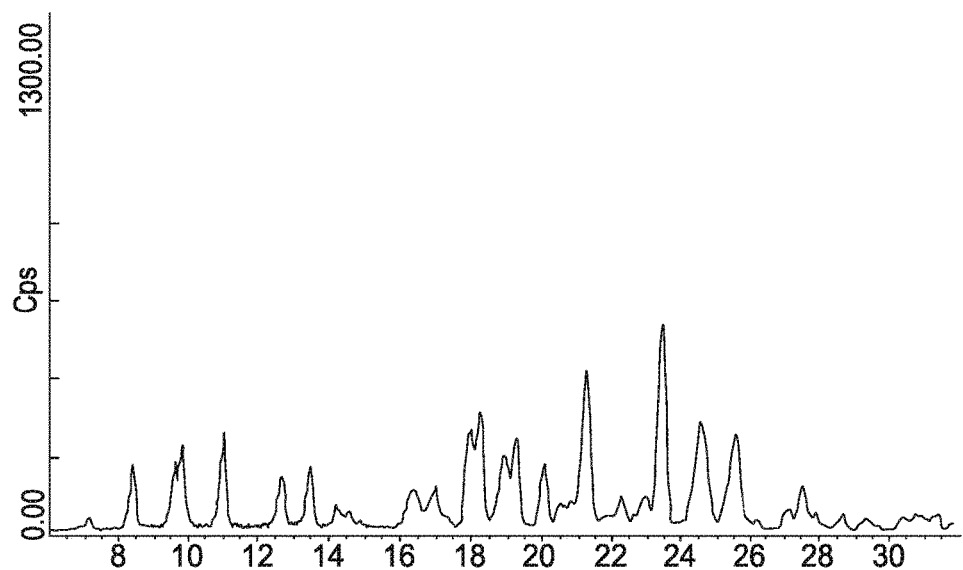

The X-ray powder patterns in FIGS. 5A-5C illustrate the crystallinity of micronised and TBS1 and TBS2 samples, which is assessed on the basis of the sharpness of the major diffraction peaks. From the results it can be seen that there is no significant difference in the XRPD profiles of micronised and TBS1 samples. However, based on XRPD data, the TBS2 sample has shown lower bulk crystallinity in comparison to the micronised sample. The DSC profiles (Table 8) confirm this conclusion; the fusion enthalpy for TBS2 batch is considerably lower than for both micronised and TBS1 batches, thus the crystallinity for TBS1 being higher than that for the micronised material.

TABLE 8

| Sample | Melting Point (° C.) | Enthalpy of Fusion (J/g) | Identification |
| --- | --- | --- | --- |
| Micronised | 266.3 | 121.76 | Form B |
| TBS 1 | 267.1 | 127.12 | Form B |
| TBS 2 | 266.3 | 88.68 | Form B |
| TBS 3 | 266.3 | 31.35 | Amorphous |
| TBS 4 | 274.5 | 40.98 | Hydrate |
| TBS 5 | 272.7 | 57.69 | Form A |

Interactions of Water h Micronised and SEDS™ Powders

The sorption and desorption isotherms of micronised and SC processed TBS show that at 25° C., the equilibrium moisture content ("moisture uptake") of all TBS samples in this study is very low (<0.4%) at any RH value. The low moisture uptake indicates that each powder is crystalline. However, TBS2 sample showed slightly higher moisture uptake than the micronised sample, which is consistent with its lower bulk crystallinity indicated by DSC and X-ray diffraction (see FIGS. 5A-5C and Table 8). Typically, an amorphous or partially crystalline material will take up more moisture than a highly crystalline material. TBS2 also takes up more moisture at relative humidities beyond 90% RH. Under these conditions, the sample may be deliquescing at high RH.

Figure 6:
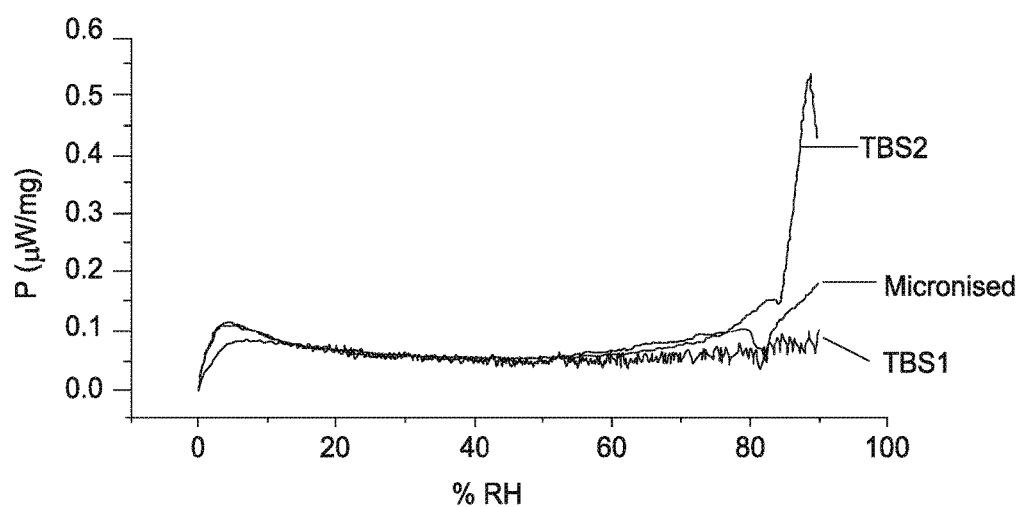
FIG. 6 depicts the heat flow (μW) for both micronised and SEDS™ powders of terbutaline sulphate.
Figure 7A:
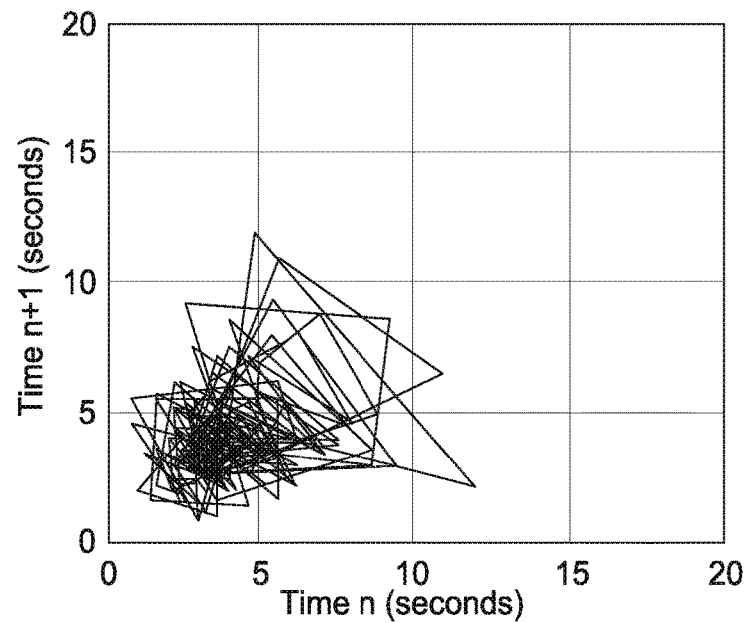
FIGS. 7A and 7B depict the strange attractor plots for terbutaline sulphate analysed at high (100 seconds per revolution) rotation speed.
Figure 7B:
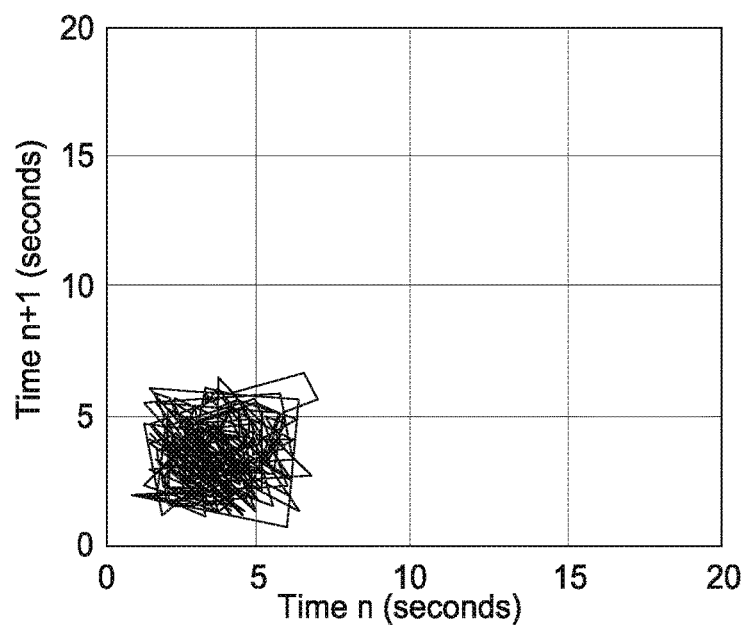
Figure 8A:
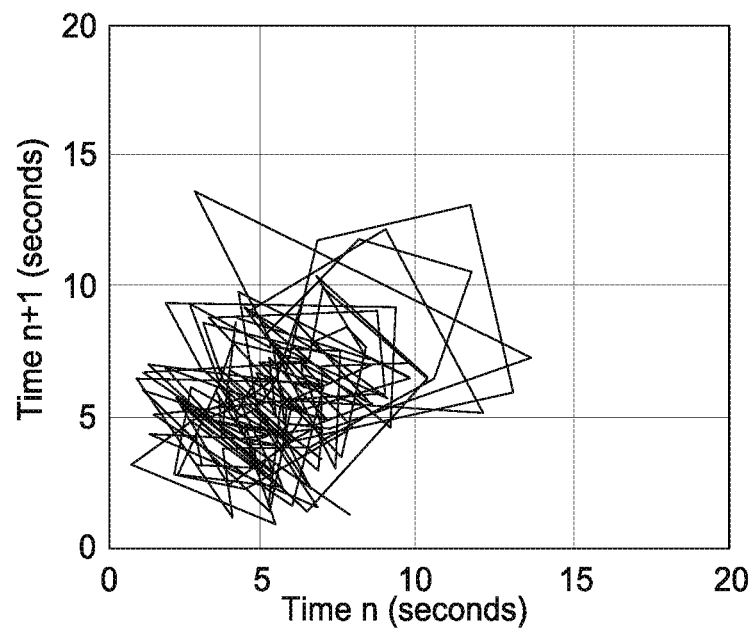
FIGS. 8A and 8B depict the strange attractor plots for TBS analysed at medium (145 seconds per revolution) rotation speed.
Figure 8B:
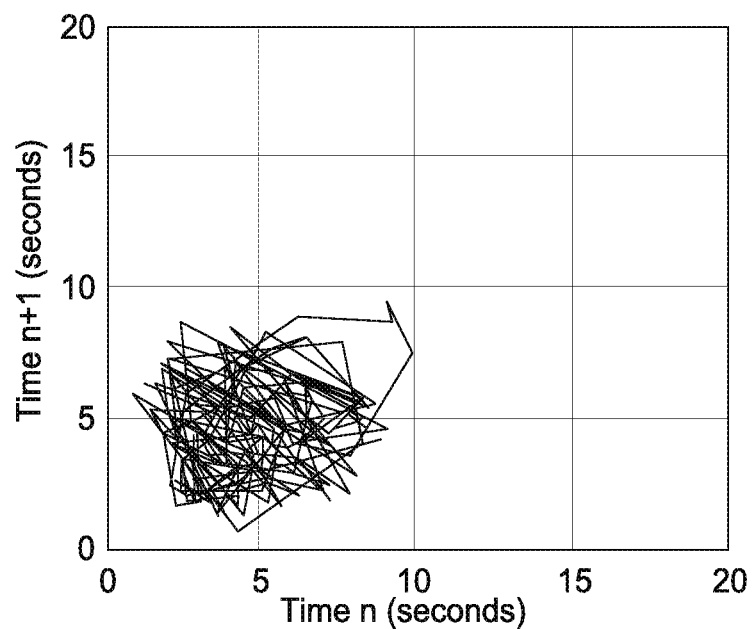

In FIG. 6, the heat flow (μW) for both micronised and SEDS™ powders of TBS are normalised to 1 mg for comparison. The endothermic peak for micronised TBS is most likely due to crystallisation of the amorphous fraction that was previously induced by micronisation. The TAM profile for TBS2 sample of TBS has an incomplete exothermic peak between 85 and 90% RH because the RH ramping experiment (3% RH/hr from 0% to 90% RH) ended before the event was completed. No exothermic or endothermic peaks were observed in the TAM profile of TBS1 sample of TBS, which is typical for a highly crystalline material. The TAM results show that the micronised TBS has an event at about 79% RH, probably due to crystallisation. The results also show that TBS2 sample has an exothermic event at about 85% RH.

Surface Energetics Properties

Micronised and supercritically processed TBS1 materials show very similar surface energetics with marginally lower non-polar, dispersive surface interaction ($\gamma_s^d$) and slightly higher specific interaction ($-\Delta G_A^{SP}$) for polar, amphoteric and basic probes. In contrast, the TBS2 sample indicated significantly less energetic, both dispersive and specific, interactions (Table 9). In addition, comparison of the $K_A$ and $K_D$ values of TBS2 and micronised samples (Table 10) indicates the weakest, both acidic and basic interactions for this supercritically processed material. Thus, the SEDS™ material has less exposed energetic acidic and basic groups. This also indicates that the surface of TBS2 particles may have a more ordered structure than that for micronised material, despite the fact that the bulk structure determined using X-ray diffraction and DSC techniques appeared more ordered for the micronised particles. Micronised material is sometimes conditioned before being used for a DPI formulation, by passing a saturated ethanol vapour through the powder bed. Similarly, TBS1 material was produced with an excess of ethanol solvent. Therefore, it is possible that the surface structure was modified after particle formation for micronised and TBS1 materials and disorganised compared to the crystal structure in the bulk.

TABLE 9

| Sample | $\gamma_s^D$ mJm$^{-2}$ | $-\Delta G_A^{SP}$ (kJ/mol) | | | | |
| --- | --- | --- | --- | --- | --- | --- |
| | | Toluene | Acetone | Ethyl acetate | Chloroform | Dioxane |
| Micronised | 58.61 | 3.42 | 12.57 | 16.01 | 1.79 | 15.96 |
| TBS 1 | 57.37 | 3.66 | 13.41 | 16.65 | 1.68 | — |
| TBS 2 | 55.05 | 2.85 | 10.42 | 13.76 | 1.21 | 14.20 |

TABLE 10

| Sample | $K_A$ | $K_D$ |
|---|---|---|
| Micronised | 0.892 | 0.051 |
| TBS 1 | 0.761 | 0.020 |
| TBS 2 | 0.778 | 0.032 |

Powder Flow Properties

For data obtained using the Aeroflow™ powder avalanching analyser, interval times between avalanches were plotted as discrete phase maps known as strange attractor plots (B. H. Kaye, J. Gratton-Liimatainen, and N. Faddis. Studying the avalanching behaviour of a powder in a rotating disc, Part. Part. Charact. 12:197-201(1995). Free-flowing powders produce strange attractor plots close to the origin with small spread, whilst, in contrast, cohesive powders give plots with a larger spread and a centroid positioned further from the origin. The strange attractor plots for TBS analysed at high (100 seconds per revolution) and medium (145 seconds per revolution) rotation speed are shown in FIGS. 7A-7B and 8A-8B, respectively.

Examination of the strange attractor plots provides a clear, visual display of the difference in flow behaviour between the micronised and TBS2. The SEDS™ sample has a lower irregularity and a lower mean avalanche time (see Table 11 and FIGS. 7A-7B and 8A-8B) compared to micronised TBS. Therefore, micronised TBS exhibits poorer flow behaviour than TBS2 material. Since a relatively large quantity (≈10 g) of powder is required to perform powder flow behaviour study, no comparison was made between TBS1 and micronised samples.

TABLE 11

| Sample | Mean time to avalanche (s) | Irregularity of flow (s) |
|---|---|---|
| Micronised (100 sec/rev) | 3.62 | 1.28 |
| Micronised (145 sec/rev) | 5.72 | 2.39 |
| TBS 2 (100 sec/rev) | 3.30 | 1.17 |
| TBS 2 (145 sec/rev) | 4.91 | 2.12 |

Enhanced flow properties of TBS2 sample are consistent with lower energetics and lower cohesiveness of this material as indicated by the IGC measurements and the following ACI studies.

Aerosol Performance of Micronised vs SEDS™ Powders

Figure 9:
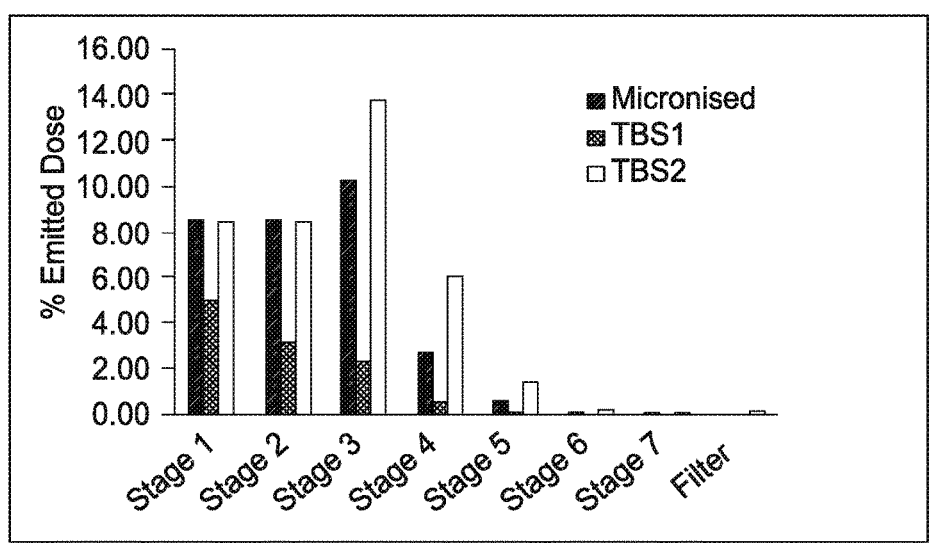
FIGS. 9 and 10 compare the in vitro performance of micronised and SEDS™ processed terbutaline sulphate analysed in a lactose blend as well as pure drug alone.
Figure 10:
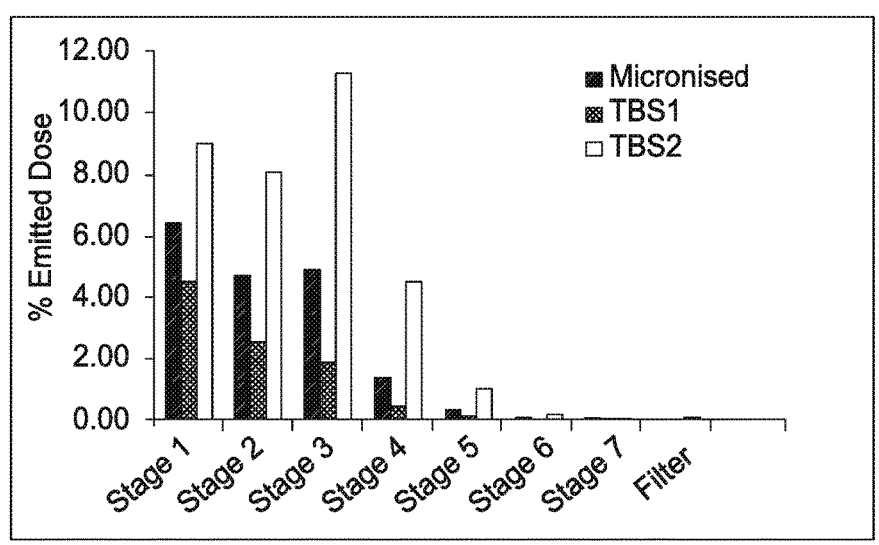

FIGS. 9 and 10 compare the in vitro performance of micronised and SEDS™ processed TBS analysed in a lactose blend as well as pure drug alone. The ACI measurements demonstrated that the TBS2 batch in both cases produced a significantly higher FPF in comparison to both micronised and TBS1 material. For this material, a high proportion of fine particle mass with a narrow distribution was collected on stage 1-3 in contrast to the broad distribution across stages 1-5 for the micronised material. The SC processed TBS2 material also demonstrated an increased fine particle fraction (FPF) in both lactose blend and drug alone compared to micronised powders (38.6% vs 30.7%, and 29.6% vs 17.7%) and increased emitted dose (see Table 12). Since the lactose particles are large and cannot penetrate beyond the pre-separator stage, this indicates that dispersion between pure drug particles and formation of loose aggregates plays a major role in defining the deposition profile.

TABLE 12

| | Total Emitted Dose (mg/dose) | | Fine Particle Fraction (%) | |
|---|---|---|---|---|
| Sample | Drug and Lactose Blend | Drug Alone | Drug and Lactose Blend | Drug Alone |
| Micronised | 80.6 | 84.2 | 30.7 | 17.7 |
| TBS 1 | 71.6 | 83.7 | 11.4 | 9.4 |
| TBS 1 | 104.8 | 98.8 | 38.6 | 29.6 |

The main factor responsible for better performance of supercritically processed TBS powder in the ACI is possibly related to the dispersibility of this powder at low air flow rates. The enhanced dispersibility is particularly significant for DPI devices where the performance strongly depends on powder deaggregation at relatively low dispersion forces. Clearly, high turbulence is favourable for dispersion but it inevitably leads to high pressure differentials which may be unacceptable for correct functioning of many devices.

Example 10

The example assessed the force of adhesion of particles of salbutamol sulphate produced using a SEDS™ processes compared to the same compound in micronised form. Conventional AFM analysis was used. Particles of the samples were mounted onto AFM probes and the adhesion force per unit area to a freshly cleaved highly oriented pyrolytic graphite substrate (HOP G, Agar Scientific, Essex, UK) in a liquid (2H 3H perfluoropentane) environment was determined. The contact area involved in the interaction was assessed and related to the force measurements.

The initial forces for individual particles of the micronised and SEDS™ produced materials were 15.77 nN (SD 4.55 nN) and 4.21 nN (SD 0.71 nN) respectively.

Following correction for surface area, the forces per unit area were 100.91 nN/$\mu m^2$ (SD 29.15 nN/$\mu m^2$) for the micronised material and 13.52 nN/$\mu m^2$ (SD 2.27 nN/$\mu m^2$) for the non-micronised SEDS™ process produced material. The particulate product of the invention clearly demonstrates lower adhesiveness than the micronised version of the same substance.

Example 11

The aerosol performance of a SEDS™ processed sample of bromocriptine mesylate was assessed in a unit-dose passive inhaler device (Turbospin PH & T (Italy)), at a peak inspiratory flow rate (PFIR) of 28.3 LPM and 60 LPM.

TABLE 13

Emitted dose performance with relative standard deviations of SEDS bromocriptine using Turbospin. Errors correspond to RSDs.

| Fill Weight (mg) | Flow Rate (LPM) | ED (%) | Left in Capsules (%) |
|---|---|---|---|
| 8.0 | 28.3 | 67.7 ± 14.7 | 10.5 ± 118 |
| | 60 | 87.5 ± 3.4 | −0.1 ± −2320 |
| 4.0 | 28.3 | 75.4 ± 3.9 | −1.5 ± −134 |
| | 60 | 83.8 ± 4.0 | 0.5 ± 347 |

The aerosol analysis (performed @60 LPM) indicated that bromocriptine yielded aerosol particles within respirable range with an aerodynamic diameter of 4.2/μm (4.3% RSD) and an improved FPF (42% of ED).

Bromocriptine dispersed well at high flow rates (ED>80%) regardless of full weight. Moreover, it exhibited minimal flow rate defendence, as ED drops were minimal (8-20%) following emptying of the capsules.

The invention claimed is:
1. An active substance in particulate form suitable for administration via a dry powder inhaler, said particulates comprising:
   a) a volume mean aerodynamic diameter of less than 7 microns;
   b) a density less than 0.5 g/ml; and
   c) a surface-to-volume ratio of at least twice that of spherical particles of the same volume diameter.
2. An active substance as in claim 1 wherein the surface-to-volume ratio is at least 2.5 times that of spherical particles of the same volume diameter.
3. An active substance of claim 1 further comprising a shape factor of at least 2.
4. An active substance of claim 1 further comprising a shape coefficient of greater than 10.
5. An active substance of claim 1 further comprising comprising an aerodynamic shape factor of at least 1.4.
6. An active substance of claim 1 further comprising a specific surface area of at least 10 m$^2$/g.
7. An active substance of claim 1 further comprising a specific surface area of at least 15 m$^2$/g.
8. An active substance of claim 1 further comprising a specific surface area of at least 20 m$^2$/g.
9. An active substance of claim 1 further comprising a specific surface area of at least 25 m$^2$/g.
10. An active substance of claim 1 further comprising a volume mean diameter of less than 6 microns.
11. An active substance of claim 1 further comprising a specific surface energy of less than 100 mJ/m$^2$.
12. An active substance of claim 1 further comprising a specific surface energy of less than 70 mJ/m$^2$.
13. An active substance of claim 1 further comprising an aggregate tensile strength less than 0.8.
14. An active substance of claim 1 further comprising a surface weighted domain size of at least 400 Å.
15. An active substance of claim 1 further comprising a volume weighted domain size of at least 700 Å.
16. An active substance of claim 1 further comprising a total strain less than $0.7 \times 10^{-3}$.
17. An active substance of claim 1 further comprising a mean specific charge from −5 to +5 nCg$^{-1}$.
18. An active substance of claim 1 further comprising a RMS roughness, measured using atomic force microscopy (AFM), of 0.5 nm or less.
19. An active substance of claim 1 further comprising a dispersive component of surface free energy, Ys$^D$, which is at least 5% lower than for the corresponding active substance made by micronization, granulation, or solvent crystallization.
20. An active substance of claim 1 further comprising a specific component of free surface energy absorption, $\Delta G_A$, which is at least 10% lower than for the corresponding active substance made by micronization, granulation, or solvent crystallization.
21. An active substance of claim 1 further comprising a mean adhesion fraction following triboelectrification in a turbula mixer which is 50% or less of that for the same active substance made by micronization, granulation, or solvent crystallization.
22. An active substance of claim 1 further comprising a theoretical aggregate tensile strength, σ, which is no more than 0.8 times that for particles of the same active substance made by a micronization, granulation, or solvent crystallization.
23. An active substance of claim 1 further comprising a particle size distribution (X$_{90}$) of from 0.5 to 10 μm.
24. An active substance of claim 1 further comprising a particle size spread, measured using a cascade impacted technique at low turbulence, which is at least 5% smaller and with a mean diameter which is at least 10% smaller than that of the corresponding active substance made by micronization, granulation, or solvent crystallization.
25. An active substance of claim 1 further comprising a total crystal strain, ε, which is at least 30% lower than that for particles of the same active substance made by micronization, granulation, or solvent crystallization.
26. An active substance of claim 1 further comprising an amorphous phase content which is at least 10 times lower than that for particles of the same active substance made by micronization, granulation, or solvent crystallization.
27. An active substance of claim 1 further comprising a mean specific charge following triboelecrification which is at least 50% lower than for the corresponding active substance made by micronization, granulation, or solvent crystallization.
28. An active substance of claim 1 further comprising a mean avalanche time as determined using a powder avalanching apparatus which is at least 5% lower at 100 s/rev than for the corresponding active substance made by micronization, granulation, or solvent crystallization.
29. An active substance of claim 1 further comprising a mean avalanche time as determined using a powder avalanching apparatus which is at least 10% lower at 145 s/rev than for the corresponding active substance made by micronization, granulation, or solvent crystallization.
30. An active substance of claim 1 further comprising an amorphous phase content of less than 1% w/w.
31. An active substance of claim 1 further comprising a bulk powder density of 0.2 g/cm$^3$ or less.
32. An active substance of claim 1 further comprising a shape factor of at least 3.5.
33. An active substance of claim 1 further comprising a root mean square (RMS) roughness, measured using atomic force microscopy, of 0.2 nm or less.
34. An active substance of claim 1 which, when delivered using a passive dry powder inhaler, yields a fine particle fraction in the emitted dose of 20% or greater.
35. An active substance according to claim 34 which yields a fine particle fraction in the emitted dose of 31% or greater.
36. An active substance according to claim 34 which yields a fine particle fraction in the emitted dose of 55% or greater.
37. An active substance according to claim 1 comprising a pharmaceutically or nutraceutically active substance.
38. An active substance according to claim 37 wherein the active substance is a pharmaceutically active substance or a mixture thereof.
39. An active substance according to claim 38 wherein the active substance is selected from the group consisting of salbutamol, terbutalene, salmeterol, fenoterol, bromocriptine or a pharmaceutically acceptable salt or mixture thereof.

40. A method of administering an active substance by inhalation comprising providing a composition according to claim 1 and administering said composition to the respiratory tract.

41. A method according to claim 40 wherein the composition is administered via a passive dry powder inhaler.

* * * * *